United States Patent [19]

Linkies et al.

[11] 4,113,874

[45] Sep. 12, 1978

[54] PYRROLIDONES, PHARMACEUTICAL COMPOSITIONS THEREWITH AND PROCESSES OF USE THEREOF

[75] Inventors: Adolf Linkies, Frankfurt am Main; Dieter-Bernd Reuschling, Butzbach; Klaus Kühlein, Kelkheim, Taunus; Gerhard Beck, Frankfurt am Main; Josef Musil, Königstein, Taunus, all of Fed. Rep. of Germany

[73] Assignee: Hoechst Aktiengesellschaft, Frankfurt am Main, Germany

[21] Appl. No.: 751,173

[22] Filed: Dec. 16, 1976

[30] Foreign Application Priority Data

Dec. 19, 1975 [DE] Fed. Rep. of Germany ....... 2557335

[51] Int. Cl.² .................. C07D 207/26; C07C 177/00
[52] U.S. Cl. ............................... 424/274; 260/326.45; 260/326.5 FL; 542/413; 542/429; 542/442
[58] Field of Search ..................... 260/326.45, 240 R; 424/274

[56] References Cited

U.S. PATENT DOCUMENTS

| | | | |
|---|---|---|---|
| 3,192,210 | 6/1965 | Lunsford | 260/326.45 |
| 3,975,399 | 8/1976 | De Franco | 260/240 R |
| 4,012,429 | 3/1977 | Sakai et al. | 260/240 R |

OTHER PUBLICATIONS

Ambrus et al., Chem. Abst., 84 (1976), #59286.
Bruin et al., Chem. Abst., 84 (1976), #121582.
Rozing, Chem. Abst., 85 (1976), #20998.
Scribner Chem. Abst., 80 (1974), #47986.
Bolliger et al., Tet. Letters, 1975 (#34), pp. 2931–2934.
Harrison et al., Tet. Letters, 1975 (#13), pp. 1165–1168.

*Primary Examiner*—Allen B. Curtis
*Attorney, Agent, or Firm*—Curtis, Morris & Safford

[57] ABSTRACT

The present application relates to novel pyrrolidones which are analogous to prostaglandins as well as to a process of preparing the same.

The new compounds have valuable pharmaceutical properties and can therefore be used as medicaments.

12 Claims, No Drawings

PYRROLIDONES, PHARMACEUTICAL COMPOSITIONS THEREWITH AND PROCESSES OF USE THEREOF

Natural prostaglandins have a carbon skeleton of, generally, 20 carbon atoms. They differ by the number of hydroxyl groups and double bonds. Since they simultaneously exhibit a plurality of physiological actions and possess only a short half-life in the organism, there are limits to their use as therapeutic agents.

The search for prostaglandins having a longer half-life and specific action is therefore becoming of increasing importance.

The present invention concerns new pyrrolidones, analogous to prostaglandins, of the formula

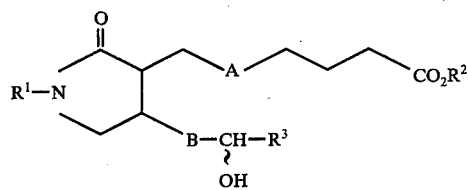
(I)

in which

A represents —CH$_2$—CH$_2$—, —CH=CH— (cis), —C≡C—,

B represents —CH=CH— (trans) or, when A = —CH$_2$—CH$_2$—, also —CH$_2$—CH$_2$—, R$^1$ represents hydrogen, a hydroxymethyl group, a phenyl radical, which in turn may be substituted one to three times by straight-chained or branched (C$_1$-C$_4$)-alkyl groups, by halogen atoms, S— or O—(C$_1$-C$_4$)-alkyl radicals, by a phenoxy group, which in turn may be substituted one to three times by optionally halogen-substituted (C$_1$-C$_4$)-alkyl groups or by halogen atoms, R$^2$ represents hydrogen, an aliphatic hydrocarbon radical having 1–5 carbon atoms, or a cycloalkyl or phenalkyl radical having 3–8 carbon atoms, R$^3$ represents a straight-chained alkyl radical having 1–10 carbon atoms, which in turn may be substituted
  a. by an O or S-alkyl radical having 1–5 carbon atoms,
  b. by a phenoxy radical, which may be substituted by one or more, optionally halogen-substituted, alkyl groups having 1–3 carbon atoms, or by halogen atoms,
  c. by an O-benzyl radical, which in turn may carry as substituents alkyl groups having 1–3 carbon atoms, or a cycloalkyl radical having 3–7 ring members or a phenyl radical, which in turn may be substituted by one or more alkyl groups having 1–3 carbon atoms, or a branched alkyl radical having 1–10 carbon atoms, which is substituted as indicated under (a) to (c) and wherein the side chains in the 3 and 4-positions of the pyrrolidone ring stand in the trans position with respect to one another, as well as the physiologically compatible metal and amine salts of the free acids.

The subject matter of the invention is furthermore a process for the manufacture of pyrrolidones of the formula I, characterised in that (a) a pyrrolidone of the formula

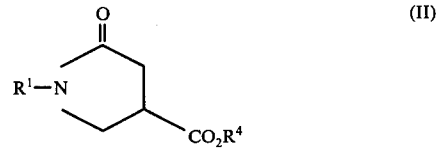
(II)

in which R$^1$ has the meaning as given for formula I, but does not represent the hydroxymethyl group, and R$^4$ represents (C$_1$-C$_4$)-alkyl, is reduced to a pyrrolidone of the formula

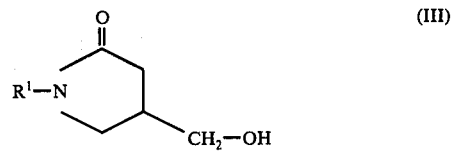
(III)

(b) the pyrrolidone of the formula III is converted into a pyrrolidone of the formula

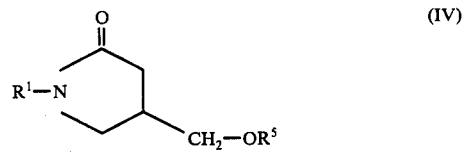
(IV)

in which R$^1$ has the meaning as given for formula II, and R$^5$ represents a protective group that can be split off easily in an acid medium, (c) the pyrrolidone of the formula IV is reacted, in the presence of a base of the formula MeB   (V)

in which Me represents an alkali metal atom and B stands for hydrogen, a (C$_1$-C$_4$)-alkyl radical, a straight-chained or branched (C$_1$-C$_4$)-alkoxy radical or a group

in which R$^6$ and R$^7$ are the same or different and represent (C$_1$-C$_4$)-alkyl or (C$_5$-C$_6$)-cycloalkyl, with a hexyne dihalide of the formula

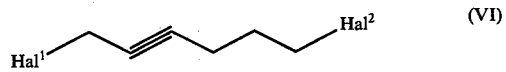
(VI)

in which either Hal$^1$ is bromine and Hal$^2$ is chlorine, or Hal$^1$ is iodine and Hal$^2$ is bromine or chlorine, to yield a compound of the formula

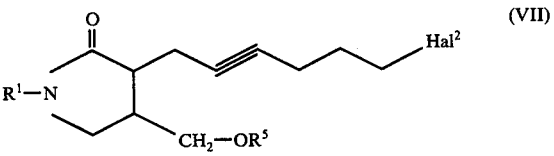
(VII)

(d) the obtained compound of formula VII is reacted with an alkali metal cyanide, whereby a cyanalkyne of the formula

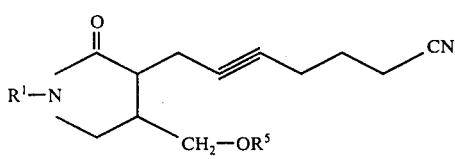

in which $R^1$ has one of the meanings given for formula II and $R^5$ represents a protective group that can be split off easily in acid medium, is obtained, (e) the obtained nitrile of the formula VIII is converted in acid medium into an ester, the protective group $R^5$ simultaneously being split off, whereby an alcohol of the formula

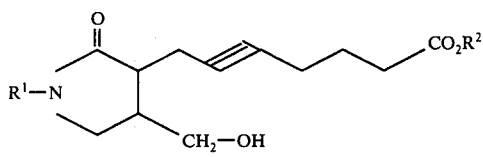

results, in which $R^1$ represents one of the radicals mentioned for formula II and $R^2$ represents a lower molecular weight alkyl radical, a cycloalkyl radical having 3-8 carbon atoms or a phenalkyl radical having 7 or 8 carbon atoms, and optionally (e') in the alcohol of the formula IX, the triple bond is partially hydrogenated to form a cis-double bond or is completely hydrogenated, whereby an alcohol of the formula

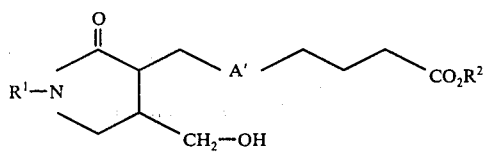

results, in which $R^1$ has one of the meanings given for the formula II and $A'$ represents —CH=CH— (cis) or —CH$_2$—CH$_2$—, (f) the alcohol obtained of the formula IX or X is oxidised, whereby an aldehyde of the formula

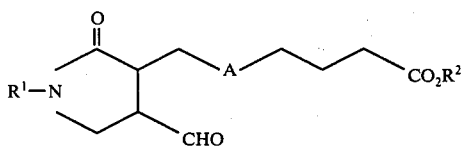

in which $R^1$ has one of the meanings given for formula II, $R^2$ one of the meanings given for formula IX and A one of the meanings given for formula I, results, (g) the obtained aldehyde of the formula XI is reacted with a phosphonate of the formula

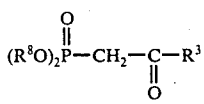 (XII)

in which $R^3$ has one of the meanings given for formula I and $R^8$ represents an unbranched ($C_1$-$C_4$)-alkyl radical, to yield a compound of the formula

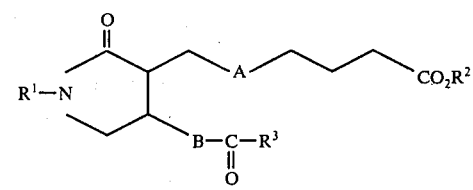

in which $R^1$ has one of the meanings given for formula II, $R^2$ has one of the meanings given for formula IX and A one of the meanings given for formula I, and B represents —CH=CH— (trans), and optionally (g') when A is a triple bond, this is partially hydrogenated to form a double bond, whereby a compound of the formula

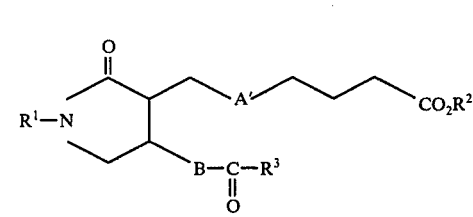

in which $R^1$ has one of the meanings given for formula II, $R^2$ one of the meanings given for formula IX and $R^3$ one of the meanings given for formula I and $A'$ is —CH=CH— (cis) and B is —CH=CH— (trans), results or (g") in the compound XIII obtained, the unsaturated C—C bonds are completely hydrogenated, whereby a compound of the formula

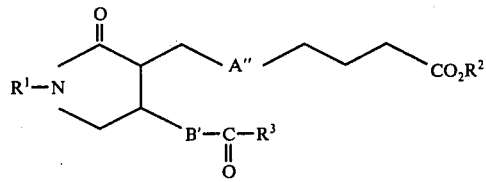

in which $R^1$ has one of the meanings given for formula II, $R^2$ one of the meanings given for formula IX and $R^3$ one of the meanings given for formula I, and $A''$ and $B'$ represent —CH$_2$—CH$_2$—, results, (h) in the obtained compound of formula XIII or of formulae XIV' and XIV", the ketocarbonyl group is reduced, whereby a compound of the formula

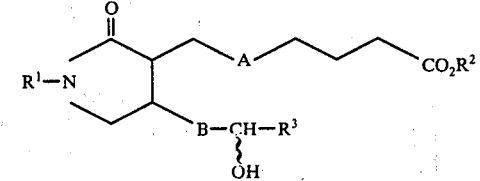

in which $R^1$ has one of the meanings given for formula II, $R^2$ one of the meanings given for formula IX, $R^3$, A and B have one of the meanings given for formula I, results, and this is optionally converted, in a manner known per se, into the free acid or its physiologically compatible metal or amine salts or (h') a compound obtained according to (h) of the formula

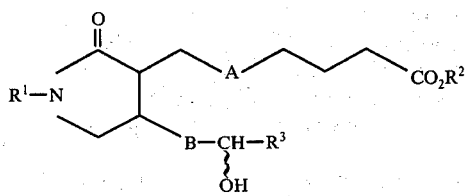

in which $R^1$ stands for hydrogen, and $R^2$, $R^3$, A and B have one of the meanings given for formula I', is reacted with formaldehyde to yield a compound of the formula I, in which R stands for —$CH_2$—OH and $R^2$, $R^3$, A and B have one of the meanings given for formula I', and this is optionally converted into the free acid or its physiologically compatible metal or amine salts.

The following substituents are preferred:

Of the meanings given for R: hydrogen, the hydroxymethyl radical, phenyl radical, toluyl radical, ethylphenyl radical, chlorophenyl radical, dichlorophenyl radical, methoxyphenyl radical, ethoxyphenyl radical or phenoxyphenyl radical, in which the phenoxy groups may be substituted in turn by one or two halogen atoms, but in particular the 4-(2',4'-dichlorophenoxy)phenyl radical.

Of the meanings given for $R^2$: saturated ($C_1$–$C_4$)-alkyl radicals, preferably the methyl radical, also cycloalkyl radicals having 5–7 carbon atoms and aralkyl radicals having 7–8 carbon atoms, in particular the benzyl radical.

Of the meanings given for $R^3$: unbranched alkyl radicals having 3–8 carbon atoms, cycloalkyl radicals having 5–7 carbon atoms as well as the phenyl radical or a phenyl radical substituted by one to three methyl groups. Furthermore, preferred meanings for $R^3$ are radicals of the formula —$C(R')_2$—$CH_2$—O—R", in which R' represents a ($C_1$–$C_3$)-alkyl radical, with the proviso that the two R' may be different, and in which R" represents a ($C_1$–$C_5$)-alkyl radical, a phenyl radical, which may be substituted by 1 or 2 fluorine, chlorine and/or bromine atoms, by the trifluoromethyl radical or by one to three ($C_1$–$C_3$) alkyl radicals or a benzyl radical, which may be substituted by one to three ($C_1$–$C_3$)-alkyl radicals.

Of the meanings given for $R^4$ in formula II, ($C_1$–$C_4$)-alkyl radicals, and in particular the methyl or ethyl radical, are preferred.

The pyrrolidones of formula II used as starting compounds in the process according to the invention, may be prepared according to processes known from the literature [A. Zilkha, E. S. Rachman, J. Rivlin, J. Org. Chem, 26, 376 (1961); K. P. Klein, H. K. Reimschuessel, J. Polym. Sci. A-1, 9, 2717 (1971); P. L. Paytash, E. Sparrow, I. C. Gathe, J. Am. Chem. Soc. 72, 1415 (1950)].

The process according to the invention begins with the conversion of the 4-alkoxycarbonyl pyrrolidones of the formula II into the 4-hydroxymethyl pyrrolidones of the formula III, which is preferably carried out with complex metal hydrides. The reduction is carried out, in particular with $NaBH_4$ with the exclusion of moisture, in an inert gas atmosphere, in ethers such as ethyleneglycol dimethyl ether or tetrahydrofuran at temperatures of between 20° and 90° C and preferably at the boiling point of the solvent. The course of the reaction is followed by thin layer chromatography (ethyl acetate/silica gel).

To isolate the hydroxymethyl compounds, the excess metal hydride is destroyed by the addition of 2N sulphuric acid, the solvent is distilled off in vacuo and the remaining residue is extracted with a suitable solvent, such as methylene chloride or chloroform. The residue remaining after the removal of the solvent is purified by recrystallisation. The working up can also be carried out by filtering off the boron compounds of the hydroxymethyl compounds produced in the reaction and subsequently decomposing them with alcohols, preferably methanol, and anhydrous acids, such as sulphuric acid. After distilling off the boric acid ester and neutralisation, the alcoholic solution of the hydroxymethyl pyrrolidone is filtered, and evaporated, and the residue is purified by recrystallisation. The introduction of the protective group $R^5$ is carried out in a manner in itself known.

There come into consideration as protective groups for the hydroxymethyl pyrrolidones chiefly those that under mild reaction conditions can be split off again, for example by acid hydrolysis or by hydrogenation. In particular, the allyl, benzyl, tert. butyl and chloromethyl radicals, as well as enol ether groups, meet this condition [E. J. Corey, J. W. Suggs, J. Org. Chem. 38, 3224, (1973); E. J. Corey, P. A. Grieco, Tetrah; Letters 107 (1972); J. F. W. McOmie, Protective Groups in Organic Chemistry, Plenum Press, London and New York, 1973, 95–143].

Preferred is the formation of acetals, which can be prepared by reacting the alcohol of the formula III with enol ethers, such as, for example, dihydropyran, in an aprotic solvent in the presence of a catalytic amount of a strong acid. There may be used as catalysts of this kind mineral acids, such as, for example, hydrochloric acid, sulphuric acid or phosphorus oxychloride or organic acids, such as p-toluenesulphonic acid or trifluoroacetic acid.

There have proved suitable as solvents for this process halogenated hydrocarbons, such as, for example, chloroform or methylene chloride, or nitriles, such as acetonitrile. The reaction is preferably carried out at 0° to 40° C. The reaction times may be from 1 to 24 hours. To isolate the compounds of the formula IV, the reaction mixture is shaken with a sufficient quantity of an acid binder, preferably with saturated sodium bicarbonate solution, the organic phase is dried with sodium sulphate and the product is purified, after the removal of the solvent by high vacuum distillation, by means of column chromatography or by recrystallisation.

The protected 4-hydroxymethyl pyrrolidones of the formula IV are deprotonated with a suitable base MeB in the α-position with respect to the carbonyl group, in the case of a pyrrolidone that is not substituted at the nitrogen both in the α-position with respect to the carbonyl group and at the nitrogen, and are subsequently reacted with an alkynyl dihalide VI, such as 1-iodo-6-bromo-hexyne(2), 1-iodo-6-chloro-hexyne(2) or preferably 1-bromo-6-chloro-hexyne(2).

The bases of the formula V are known from the literature. Me represents an alkali metal, lithium, sodium or potassium being preferred.

When B represents the radical

then there come into consideration for $R^6$ and $R^7$ straight-chained or branched $(C_1-C_6)$-alkyl radicals, such as, for example, methyl, ethyl, propyl, pentyl, hexyl, preferably isopropyl, or in the case of a $(C_3-C_6)$-cycloalkyl group, for example cyclopropyl, cyclobutyl, cyclopentyl, and in particular cyclohexyl. Particularly preferred as compounds of the formula V are butyl lithium, sodium hydride, potassium-tert.-butylate, lithium diisopropylamide and lithium cyclohexylisopropylamide.

The reaction of the base V with the compounds of the formula IV is, on account of the sensitivity to air and moisture of the bases and the resulting carbanions, carried out with the exclusion of air and moisture. There come into consideration as solvents, in particular aprotic polar liquids that even at low temperatures still possess an adequate dissolving power and are inert under the reaction conditions. Optionally mixtures of two or more solvents are used to reduce the solidification point. Preferred are, for example, ethers, such as dimethyl ether, diethyl ether, diisopropyl ether, tetrahydrofuran, glycoldimethyl ether, and also dimethyl formamide, dimethyl sulphoxide, tetramethylethylene diamine or also toluene. The quantities of the solvent are to be so measured that the solutions are homogeneous in each case.

The reaction temperatures lie between −100° and +10° C, preferably between −80° and 0° C, in particular between −70° and −10° C. The reaction is generally carried out by adding a solution of the pyrrolidone of formula IV to a low-temperature solution of the base V in one of the said solvents while stirring, in such a manner that the temperature range desired for the reaction is observed. The combination of the components can also take place in the reverse order.

Subsequently, the low-temperature solution thus obtained is added to a low-temperature solution of approximately equimolar quantities of the alkynyl halide of the formula VI [Lit: A. J. Rachlin, N. Wasyliw and M. W. Goldberg, J. Org. Chem. 26, 2688 (1961)] again in such a manner that the mentioned temperature range of the reaction mixture is not substantially exceeded as a result of the exothermic reaction. There is suitable as solvent in each case one of those already mentioned.

The combination of the components can also take place in the reverse order.

Once the addition is complete, stirring is continued for a further half hour to 12 hours at low temperature, and then the mixture is worked up. The working up can be carried out by adding to the reaction mixture a particular quantity of water, separating the organic phase, then drying and concentrating it. The residue can be purified by column chromatography. Often the products which result are already so pure that purification is not necessary.

To prepare the nitriles of the formula VIII, an alkali cyanide is dissolved in a solvent mixture such as ethanol/water, dimethyl formamide/water or preferably in pure dimethyl sulphoxide, and the halogen compund of the formula VII, dissolved in the same solvent, is added dropwise at 60°-120° C, in particular between 80° and 90° C, to the alkali cyanide solution. Once the addition is complete, stirring is continued for 2-8 hours at 80°-90° C. The isolation of the nitriles of the formula VIII is carried out, for example, by adding water to the reaction mixture and extracting the aqueous phase with an organic solvent that is not water-miscible. The resulting products are frequently so pure that they can be used for the next reaction steps without further purification. If necessary they are purified by column chromatography.

The ester of the formula IX is obtained directly from the nitrile of the formula VIII, by dissolving the latter in an excess of alcohol, saturating the solution at +5° to −20° C, preferably at 0° to −5° C with dry hydrogen chloride gas, and after approximately 2 to 4 hours removing the solvent and the excess hydrogen chloride carefully in vacuo, taking it up again in alcohol, adjusting the pH value to 1-4, preferably 1-2, with 33% aqueous alkali hydroxide solution, and subsequently heating at 60°-80° C for 0.5-3 hours. The isolation of the esters of the formula IX is effected, for example, by removing the solvent and subsequently extracting the residue with an organic solvent. Then, a chromatographic purification of the ester IX is recommended.

The stereoselective, partial hydrogenation of the compounds of the formula IX to the compounds of the formula X with a cis-double bond can be carried out by processes known per se (H. C. Brown: Hydroboration, W. A. Benjamin Inc., New York 1962; Houben-Weyl, Methoden der organischen Chemie, Georg Thieme Verlag, Stuttgart 1970, Vol. XIII/4, pages 135-41, 206: loc. cit. vol. V/Ib. 1972, page 585 ff.).

Preferably the catalytic hydrogenation is at room temperature with reduced palladium catalysts, in particular with palladium on calcium carbonate (10% Pd) in the presence of quinoline. Methanol, ethanol, glacial acetic acid and ethyl acetate, but preferably benzene, are used as solvent.

For isolation, the catalyst is filtered off and the filtrate worked up in the usual manner, for example by distilling off the solvent.

The complete hydrogenation of the triple bond of the compounds of formula IX to the saturated compounds of formula X can be carried out by methods known per se (F. Zymalkowski, Katalystische Hydrierungen, Ferdinand Enke Verlag, Stuttgart 1965, page 42 ff, Houben-Weyl: Methoden der organischen Chemie, Georg Thieme Verlag, Stuttgart 1970, Vol V/1a, 1972, page 7 ff.). The catalytic hydrogenation at room temperature with platinum catalysts, in particular with platinum black, is preferred. Ethyl acetate, glacial acetic acid, but preferably methanol and ethanol, are used as solvent.

To isolate the reaction product, the catalyst is filtered off and the filtrate worked up in the usual manner, for example by distilling off the solvent.

The partial hydrogenation of the triple bond and the complete hydrogenation can be carried out in a similar manner also at the later stages XIII and I. The oxidation of the compounds of the formulae IX and X to the compounds of the formula XI is effected with oxidising agents that are customary for the oxidation of aliphatic alcohols to aldehydes. Some of these customary methods are described in Houben-Weyl, Vol. VII/1, page 159. Further suitable oxidising agents are the complexes formed from thioethers, such as dimethyl sulphide or thioanisol, with chlorine or N-chlorosuccinimide [E. J. Corey, C. U. Kim, J. Am. Chem. Soc. 94, 7586 (1972); E. J. Corey, C. U. Kim, J. Org. Chem. 38, 1233 (1973)].

In addition, oxidation with dimethyl sulphoxide can be carried out under a wide variety of conditions [W. W. Epstein, F. W. Sweat, Chem. Rev. 67, 247 (1967)] or oxidation can be effected with chromic acid in dimethyl sulphoxide [Y. S. RaO, R. Filler, J. Org. Chem. 39, 3304 (1974)].

A particularly preferred process is oxidation with the chromium trioxide-pyridine complex (J. C. Collins, Tetrah, Letters 1968, 3363). First of all the complex is prepared in an inert solvent, preferably methylene chloride, then a solution of alcohol is added at $-10°$ to $+10°$ C. The oxidation proceeds rapidly and is usually complete after 5 to 30 minutes.

The aldehyde of the formula XI can be used without further purification for the next process stop. If necessary the aldehyde is purified by column chromatography.

The reaction of the phosphonates of the formula XII with compounds of the formula XI can be carried out under the conditions customary for the Horner reaction, for example in ethers at room temperature. There are preferred as ethers, diethyl ether, tetrahydrofuran and dimethoxyethane. The phosphonate is, to make the reaction more complete, used in an excess of up to double the equivalent amount. The reaction is usually complete after 1–5 hours at room temperature. The reaction product of the formula XIII is then isolated from the reaction mixture by the usual processes and purified by column chromatography.

The phosphonates of the formula XII are either known [D. H. Wadsworth et al., J. Org. Chem. 30, 680 (1965)] or can be prepared analogously to known methods. That which was said concerning the hydrogenation of IX applies for the hydrogenation of XIII.

Compounds of the formula I are obtained by treating the compounds of the formula XIII or XIV with a reducing agent. The reduction can be carried out with any reducing agent that renders possible a selective reduction of a keto group to a hydroxyl group. Preferred reducing processes are those that use sodium borohydride, zinc borohydride or lithiumperhydro-9b-boraphenalkyl hydride [H. C. Brown, W. C. Dickason, J. Am. Chem. Soc. 92, 709 (1970)]. Usually the reduction is carried out between 0° and 50° C in a solvent that is inert with respect to the hydrides, such as diethyl ether, dimethoxyethane, dioxane, tetrahydrofuran or diethyleneglycol dimethyl ether.

Furthermore, the method according to Meerwein-Ponndorf-Verley belongs to the preferred processes, in which the ester function can, of course, enter into a transesterification reaction with the alcohol used as reducing agent [T. Bersin, "Neuere Methoden", Vol. 1, pages 137–154 (1949); A. L. Wilds, Org. Reactions 2, 178 (1944)].

The diastereoisomers resulting in this reduction process can be separated by means of the usual methods, such as thin layer or column chromatography. Their conversion into the free acids is effected by one of the current hydrolytic methods.

The manufacture of pharmacologically compatible salts from the acids is carried out in the usual manner. The acid is dissolved in a solvent, such as water, methanol, tetrahydrofuran, neutralised with the appropriate inorganic or organic base, and then, if the salt does not precipitate, a solvent of suitable polarity, such as methanol, ethanol, or dioxane is added, or the solution is evaporated to dryness.

Of the inorganic bases the alkali metal and alkaline earth metal hydroxides are preferred. Of the organic bases there come into consideration, primary, secondary and tertiary amines, such as, for example, methyl, dimethyl, trimethyl, and phenylethyl amine, ethylene diamine, allylamine, piperidine, morpholine and pyrrolidine. Also amines that in addition contain hydrophilic groups, such as ethanolamine and ephedrine, come into consideration. Suitable quaternary bases are, for example, tetramethyl ammonium hydroxide and benzyltrimethyl ammonium hydroxide.

The preparation of N-hydroxymethyl compounds of formula I from the unsubstituted pyrrolidones (R = H, $R^2 \neq H$) is carried out according to known processes [A. Ginhorn, Frdl. Fortschr. Teerfarben Fabrikat. 7, 616 (1902–1904)]. For this, the compounds of formula I' that are not substituted at the nitrogen, or the salts thereof, are dissolved in a suitable solvent, such as methanol or ethanol or mixtures thereof with water or water itself, but preferably methanol, and formaldehyde or a suitable formaldehyde source, such as paraformaldehyde, but preferably formalin, is added, and an alkali hydroxide or alkali carbonate is added as catalyst. Working up, and if desired conversion into the free acid, is effected according to methods known per se.

The esters of formula I, the acids forming the bases thereof, and the salts that can easily be produced therefrom exhibit prostaglandin-like actions. The new compounds exhibit luteolytic, gastric juice secretion-inhibiting, bronchospasmolytic and/or antihypertensive properties. Furthermore, the new compounds of the invention can also be used as and are valuable as intermediate products for the production of other substances having a prostaglandin action.

The following single and daily dosages come into consideration for the various possible indications:

Bronchodilatory action (in the form of an aerosol)

Single dose: 0.1 - 1000 μg
preferred: 1 - 200 μg (per burst of spray)
daily dosage: 0.1 - 10 mg Blood pressure reducing action Single dose: 1 - 1000 μg
preferred: 1 - 100 μg parenteral (intravenous)
daily dosage: 1 - 10 mg oral
single dose: 0.5 - 1000 μg
preferred: 1 - 500 μg oral
daily dosage: 1 mg- 10 mg The doses when using against gastro-intestinal disturbances correspond to those when used as a blood pressure reducing agent.

The compounds of the formulae VII, VIII, IX, X, XI, XIII and XIV are new valuable intermediate products for the manufacture of the compounds of formula I.

EXAMPLE 1

4-Hydroxymethylpyrrolidone (2)

40 g (1 mol) of pulverised sodium boranate are added, while stirring, to 100 g (0.7 mol) of 4-carbomethoxypyrrolidone (2) in 700 ml of dimethoxyethane in a 2 liter flask. Over the next hour the temperature is held at 30° to 35° C, if necessary by cooling. Over the course of the following hour the whole is heated gradually to boiling. Then the agitator is switched off and boiling under reflux is carried out for 6 hours. After cooling, the dimethoxyethane is poured off from the reaction product and the latter is taken up in 2.5 l of methanol. As a result hydrogen is evolved vigorously and efficient cooling is recommended. After the reaction has calmed down, acidification is carried out with concentrated $H_2SO_4$ and liquid is distilled over until a sample of the distillate burns with a faint green color only (boron test).

The solution is then neutralised with solid potassium carbonate and filtered. The syrup remaining after concentration is thoroughly extracted by boiling 3 times with 1 liter of acetone each time. The acetone is concentrated to 200 ml and cooled to 0° C. 76.5 g of 4-hydroxymethylpyrrolidone crystallise out, and are suction-filtered and dried. Melting point: 95°-96° C (acetone; isopropanol)

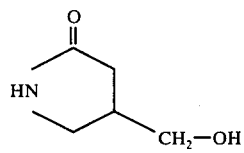

EXAMPLE 2

4-Hydroxymethyl-1-phenylpyrrolidone (2)

12 g (0.3 mol) of sodium boranate are added in portions, while stirring, to 42.8 g (0.2 mol) of 4-carbomethoxy-1-phenylpyrrolidone (2) in 200 ml of dimethoxyethane, and the whole is boiled for 12 hours. After cooling, the solvent is poured off, the residue taken up in methylene chloride and 2N $H_2SO_4$ is added thereto until acid reaction. After separating the methylene chloride, it is deacidified with sodium hydrogen carbonate solution and dried with sodium sulphate. The residue remaining after removing the solvent in vacuo is dissolved in a little ethanol and cooled to 0° to +5° C.

31.4 g of 4-Hydroxymethyl-1-phenylpyrrolidone crystallise out, and this is suction filtered and washed with a little ice-cold ethanol and dried.

Melting point: 80°-83° C (ethanol); boiling point: 180°-182° C at 0.2 mm Hg.

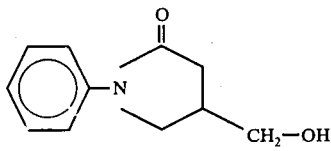

EXAMPLE 3

4-Hydroxymethyl-1-[4-(2',4'-dichlorophenoxy)-phenyl]-pyrrolidone(2)

2.2 g (55 mmol) of pulverised sodium boronate are added, while stirring, to 38 g (100 mmol) of 4-carbomethoxy-1-[4-(2',4'-dichlorophenoxy)-phenyl]-pyrrolidone(2) in 200 ml of dimethoxyethane, and the whole is boiled for 6 hours. After cooling, acidification is carried out with 2N HCl and extraction is carried out 3 times with methylene chloride. After diacidifying the methylene chloride with aqueous sodium bicarbonate solution, and drying over sodium sulphate, the solvent is removed and the residue is dissolved in a little ethyl acetate. On cooling, 13 g of 4-hydroxymethyl-1-[4-(2',4'-dichlorophenoxy)-phenyl]-pyrrolidone(2) crystallise out, which is filtered off, washed with a little ethyl acetate and subsequently dried. Melting point: 104°-108° C (ethyl acetate/hexane)

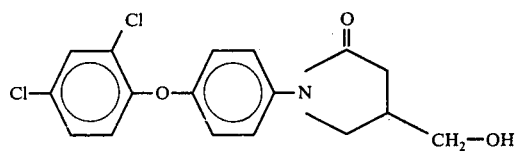

EXAMPLE 4

4-(2-Tetrahydropyranyl-oxymethyl)-pyrrolidone(2)

76.5 g (665 mmol) of 4-Hydroxymethylpyrrolidone (2), 70 g (833 mmol) of dihydropyran in 400 ml of methylene chloride and 4 g of p-toluenesulphonic acid are boiled for 4 hours while stirring vigorously. During the course of this the alcohol gradually goes into solution. After cooling the mixture is poured while stirring well, into excess, ice-cold sodium bicarbonate solution. After separating the methylene chloride phase, drying over sodium sulphate and removing the solvent in vacuo, distillation is carried out. The 4-(2-tetrahydropyranyl-oxymethyl)-pyrrolidone(2) distills over at 0.2 mm Hg and 150°-160° C and gradually solidifies.

Melting point: 23°-26° C.

$n_D20$: 1.4970

Rf: 0.16 (ethyl acetate)

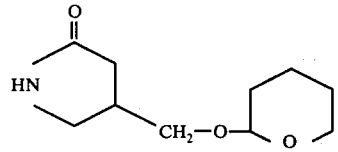

EXAMPLE 5

1-Phenyl-4-(2-tetrahydropyranyl-oxymethyl)-pyrrolidone (2)

1 drop of concentrated hydrochloric acid and 1 drop of water are added to a suspension of 60 g (0.31 mol) of 1-phenyl-4-hydroxymethylpyrrolidone(2) in 100 ml of methylene chloride and 170 g (2.0 mol) of dihydropyran. After 16 hours at room temperature, the mixture is poured into excess sodium bicarbonate solution. The methylene chloride solution is separated off, washed with water and dried over sodium sulphate. After distilling off the methylene chloride and the excess dihydropyran, the syrup is taken up in hexane and a little ethyl acetate. The crystals that separate out are suction filtered, washed with hexane and dried.

Melting point: 60°-64° C.

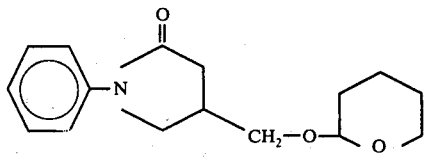

EXAMPLE 6

1-4-(2',4'-Dichlorophenoxy)-phenyl]-4-(2-tetrahydropyranyloxymethyl)-pyrrolidone(2)

is obtained in a manner analogous to that in Example (5) by using 4-hydroxymethyl-1-[4-(2',4'-dichlorophenoxy)-phenyl]-pyrrolidone(2).

Melting point: 105°–106° C (ethyl acetate)

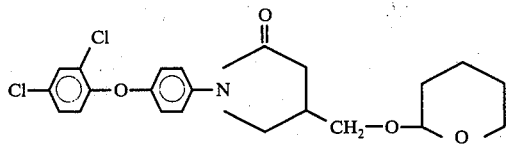

EXAMPLE 7

1-Phenyl-3-[6-carbomethoxy-2-hexyn-yl(1)]-4-hydroxymethylpyrrolidone(2)

(a) 27.5 g (100 mmol) of 1-phenyl-4-(2-tetrahydropyranyloxymethyl)-pyrrolidone(2) dissolved in 50 ml of tetrahydrofuran are added while stirring at −70° C, to 105 mmol of lithium diisopropylamide in 50 ml of tetrahydrofuran over a period of 20 minutes. After stirring subsequently for 45 minutes, the solution is introduced into a coolable dropping funnel (−35° to −45° C) and while stirring added dropwise in 60 minutes to a solution, held at −70° C, of 20.5 g (105 mmol) of 1-bromo-6-chloro-hexyne(2) in 50 ml of ether. After stirring subsequently for 90 minutes, the mixture is heated slowly to room temperature, 50 ml of water is added, the organic phase is separated off, and the aqueous phase is extracted three times with 50 ml of diethyl ether each time. The combined ether phases are washed three times with 30 ml of cold 1N sulphuric acid each time, once with 30 ml of saturated sodium bicarbonate solution and once with 30 ml of water. After drying and evaporating the ether solution, 37 g. of crude 1-phenyl-3-[6-chloro-2-hexyne-yl-(1)]-4-(2-tetrahydropyranyloxymethyl)-pyrrolidone, which is used for the next reaction stage without further purification, are obtained. Rf: 0.42 (toluene/ethyl acetate = 8 : 2)

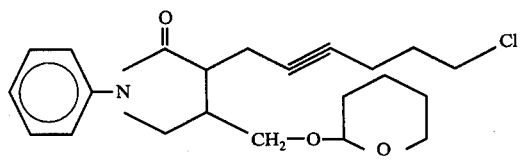

(b) 3.3 g (65 mmol) of sodium cyanide are placed in 45 ml of dimethyl sulphoxide and heated to 80° C. While stirring, 22.0 g (56.5 mmol) of crude 1-phenyl-3-[6-chloro-2-hexyn-yl(1)]-4-(2-tetrahydropyranyl-oxymethyl)-pyrrolidone(2), dissolved in 20 ml of DMSO, are added dropwise. Subsequently the mixture is stirred for 3-6 hours at 80° C. The course of the reaction is followed by thin layer chromatography (ethyl acetate/toluene =2 : 8). When the reaction is complete the mixture is cooled to 10° C, 100 ml of water are added, and extraction is carried out three times with 100 ml of diethyl ether each time. The combined ether phases are washed three times with saturated sodium chloride solution and dried. After concentrating in vacuo, 20.2 g of crude 1-phenyl-3-[6-cyano-2-hexyn-yl(1)]-4-(2-tetrahydropyranyl-oxymethyl)-pyrrolidone(2), which can be used without further purification for the next reaction, are obtained.

Rf: 0.39 (toluene/ethyl acetate = 8 : 2)

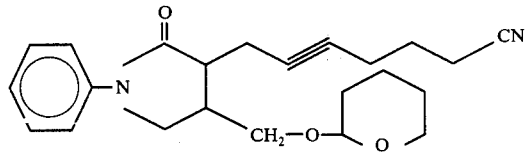

(c) 20.2 g (53.2 mmol) of 1-phenyl-3-[6-cyano-2-hexyn-yl(1)]-4-(2-tetrahydropyranyl-oxymethyl)-pyrrolidone are dissolved in 60 ml of absolute methanol and 120 ml of diethyl ether, the solution is saturated at 0° to −5° C with hydrogen chloride gas and subsequently stirred at this temperature for 2–3 hours. Subsequently the excess hydrogen chloride and the solvent are removed at 0° to 20° C in vacuo. The residue is taken up in 100 ml of methanol and the solution is adjusted with 33% aqueous sodium hydroxide solution, while cooling with ice, to a pH of 1.5–2. Boiling under reflux is then carried out for 50–60 minutes. To work up, the methanol is distilled off in vacuo, 30 ml of water are added to the residue and the resulting ester is extracted with methylene chloride. The purification is carried out by column chromatography (silica gel/ethyl acetate). 15 g of 1-phenyl-3-[6-carbomethoxy-2-hexyn-yl(1)]-4-hydroxymethyl-pyrrolidone(2) are obtained.

Rf: 0.72 (ethyl acetate)

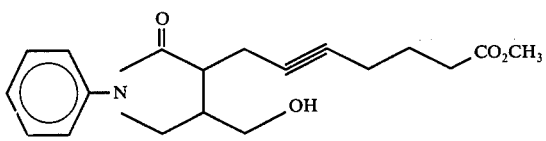

EXAMPLE 8

1-[4-(2',4'-Dichlorophenoxy)-phenyl]-3-[6-carbomethoxy-2hexyn-yl(1)]-pyrrolidone(2)

is obtained in a manner analogous to that in Example (7) starting from 1-[4-(2',4'-dichlorophenoxy)-phenyl]-4-(2-tetrahydropyranyloxymethyl)-pyrrolidone(2) (Example 6).

Melting point: 79°–80° C (ethyl acetate)

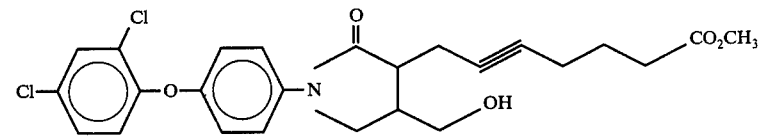

EXAMPLE 9

3-[6-Carbomethoxy-2-hexyn-yl(1)]-4-hydroxymethyl-pyrrolidone(2)

(a) 0.68 mol of butyl lithium in hexane (2N) is added while stirring at −15° C, to 67 g, (0.34 mol) of 4-(a2-tetrahydropyranyloxymethyl)-pyrrolidone(2) in 500 ml of absolute tetrahydrofuran and 3 ml of hexamethylphosphoric acid trisamide. After stirring for 5 hours at −15° C, the mixture is left overnight at this temperature and cooled the next morning to −70° C. Then, at this temperature, 70.4 g (0.36 mol) of 1-bromo-6-chloro-hexyne(2) in 50 ml of tetrahydrofuran are added dropwise over a period of 15 minutes. The mixture is then allowed to warm up to 0° C and then stirred for 40 minutes at this temperature. It is then cooled to −10° C and while stirring well, 165 ml of 2N sulphuric acid are added dropwise at this temperature. Subsequently the tetrahydrofuran is distilled off in a rotary evaporator and the aqueous phase is extracted three times with 200 ml of ether each time. After washing the ether phases with water and drying over sodium sulphate, the ether is removed in vacuo and 110 g of crude 3-[6-chloro-2-hexyn-yl(1)]-4-(2-tetrahydropyranyloxymethyl)-pyrrolidone(2), which can be used without purification for the next reaction, are obtained.

Rf: 0.57 (ethyl acetate)

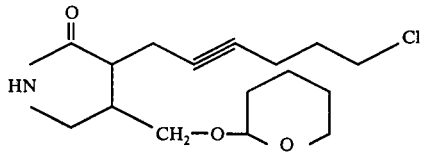

(b) 24.5 g (0.5 mol) of sodium cyanide are introduced into 270 ml of DMSO and the whole is heated to 80° C. 110 g of crude 3-[6-chloro-2-hexyn(1)yl]-4-(2-tetrahydropyranyl-oxymethyl)-pyrrolidone(2) in 100 ml of DMSO are added dropwise while stirring. Subsequently stirring is carried out for 3≧6 hours at 80° C. The course of the reaction is followed by thin layer chromatography (ethyl acetate). Once the reaction is complete, the mixture is cooled to 10° C, 600 ml of water are added and extraction is carried out five times with 200 ml of diethyl ether each time. The combined ether phases are washed three times with saturated sodium chloride solution and dried. After concentrating in vacuo, 75 g of crude 3-[6-cyano-2-hexyn-yl(1)]-4-(2-tetrahydropyranyl-oxymethyl)-pyrrolidone(2), which can be used without purification for the next reaction, are obtained.

RF: 0.53 (ethyl acetate)

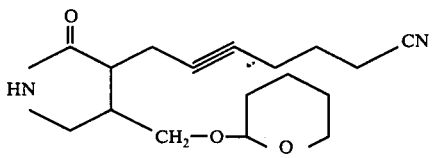

(c) 75 g of crude 3-[6-cyano-2-hexyn-yl(1)]-4-(2-tetrahydropyranyloxymethyl)pyrrolidone(2) are dissolved in 500 ml of diethyl ether and 250 ml of absolute methanol, the solution is saturated at 0° to −5° C with hydrogen chloride gas, and the whole is stirred for 2-3 hours at this temperature. A thin layer chromatography check (silica gel, CHCl₃; CH₃OH = 9 : 2) shows that the tetrahydropyranyl radical is split off in a few minutes and the nitrile is in 2-3 hours completely converted into the imidoether-hydrochloride.

Subsequently the excess hydrogen chloride and the solvent are removed in vacuo at 0° to +20° C. The residue is taken up in 400 ml of methanol and the solution is adjusted with 33% aqueous sodium hydroxide solution, while cooling with ice, to a pH of 1.5-2. For complete hydrolysis of the imidoetherhydrochloride, the solution is boiled under reflux for 1-2 hours. A thin layer chromatography check is carries out with silica gel/acetone. To work up, the methanol is distilled off in vacuo 50 ml of water are added to the residue, and the resulting ester is extracted eight times with 100 ml of methylene chloride each time. The purification is carried out by column chromatography (silica gel/acetone). 28 g of 3-[6-carbomethoxy-2-hexyn-yl(1)]-4-hydroxymethy-pyrrolidone(2) are obtained.

Rf: 0.26 (ethyl acetate)

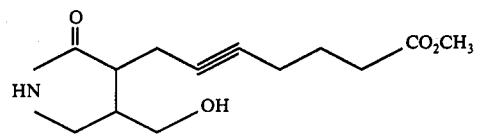

EXAMPLE 10

3-[6-Carbomethoxy-hexan-yl(1)-4-hydroxymethyl-pyrrolidone(2)

5 g (19.8 mmol) of the 3-[6-carbomethoxy-2-hexyn-yl(1)]-4-hydroxymethyl-pyrrolidone(2) obtained according to Example (9) are dissolved in 100 ml methanol and 200 ml of platinum dioxide are added thereto. Then stirring is carried out while introducing hydrogen, until hydrogen absorption is complete. Subsequently the catalyst is filtered off and the solution is evaporated in vacuo. To remove small impurities, the crude product is purified by column chromatography (silica gel/acetone). 4.5 g of 3-[6-Carbomethoxy-hexan-yl(1)]-4-hydroxymethylpyrrolidone(2) are obtained.

Rf: 0.14 (ethyl acetate)

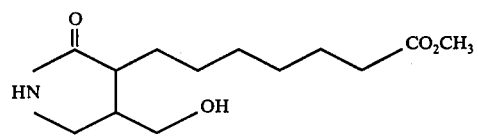

EXAMPLE 11

1-Phenyl-3-[6-carbomethoxy-hexan-yl(1)]-4-hydroxymethyl-pyrrolidone(2)

is obtained in a manner analogous to that in Example (10) using 1-phenyl-3-[6-carbomethoxy-2-hexyn-yl(1)]-4-hydroxymethyl-pyrrolidone(2). The column chromatography is carried out with silica gel/ethyl acetate (2:1).

Re: 0.74 (ethyl acetate/hexane = 1 : 1).

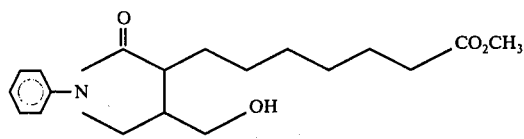

EXAMPLE 12

1-[4-(2',4'-Dichlorophenyoxy)-phenyl]-3-[6-carbomethoxy-hexan-yl(1)]-4-hydroxymethyl-pyrrolidone(2)

is obtained in a manner analogous to that in Example (10) using 1-[4-(2',4'-dichlorophenyoxy)-phenyl]-3-[6-carbomethoxy-2-hexyn-yl(1)]-4-hydroxymethyl-pyrrolidone(2) (Example 8). Melting point: 82° – 83° C (ether)

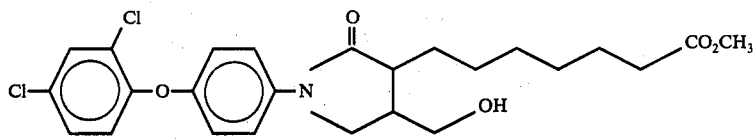

EXAMPLE 13

1-Phenyl-3-[6-carbomethoxy-(Z)-2-hexen-yl(1)]-4-hydroxymethyl-pyrrolidone(2)

3.0 g of 1-Phenyl-3-[6-carbomethoxy-2-hexyn-yl(1)]-4-hydroxymethyl-pyrrolidone(2) are dissolved in 50 ml of benzene and 0.8 ml of quinoline as well as 0.2 g of palladium on calcium carbonate (type E 40 N, Degussa) are added thereto. The whole is stirred while introducing hydrogen, until the theoretical quantity of hydrogen is consumed. Then the catalyst is filtered off, the quinoline is extracted by shaking with 2N $H_2SO_4$, the benzene solution is dried and evaporated. The residue is purified by column chromatography (silica gel/ethyl acetate).

Rf: 0.31 (ethyl acetate/hexane)

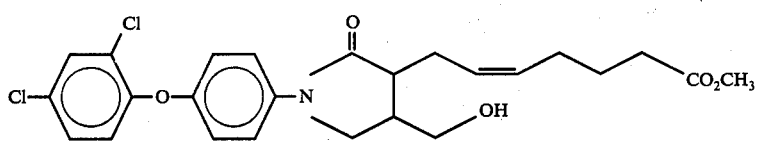

EXAMPLE 14

3-[6-Carbomethoxy-2-hexyn-yl(1)]-4-[3-oxo-(E)-1-octen-yl(1)]-pyrrolidone (2)

(a) 8.3 g (83 mmol) of chromium trioxide are introduced in portions, while stirring, into a solution of 13.2 g (166 mmol) of pyridine in 200 ml of methylene chloride, at room temperature. Stirring is continued for 20 minutes at room temperature, the mixture is cooled to 0° C and there is added thereto, dropwise, over a period of 10 minutes, a solution of 2.53 g (10 mmol) of 3-[6-carbomethoxy-2-hexyn-yl(1)]-4-hydroxymethyl-pyrrolidone (2) in 25 ml of absolute methylene chloride. After a further 30 minutes, 75 ml of 2N sulphuric acid are added, the organic phase is separated, dried and evaporated in vacuo at a bath temperature of 30° C maximum. 2.0 g of crude 3-[6-carbomethoxy-2-hexyn-yl(1)]-4-formyl-pyrrolidone(2), which can be used without further purification for the next reaction, are obtained.

Rf: 0.22 (ethyl acetate)

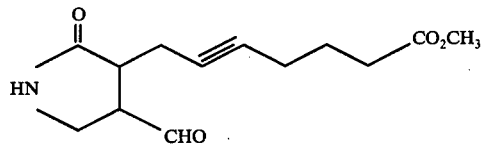

(b) At −70° C, 10 mmol of butyl lithium in hexane (2N) are added dropwise to a solution of 3.06 g (10 mmol) of dibutyl-(2-oxoheptyl)-phosphonate in 30 ml of absolute dimethoxyethane. After stirring for 15 minutes, 2.0 g of crude 3-[6-carbomethoxy-2-hexyn-yl(1)]-4-formyl-pyrrolidone(2) in 20 ml of dimethoxyethane are added dropwise. Then the whole is stirred for 2 hours at +20° C, acidified with 2N sulphuric acid (pH of 3–5), and the solution is concentrated in vacuo and the reaction product extracted five times by shaking with methylene chloride. The methylene chloride is dried and concentrated to a syrup. The purification of 3-[6-carbomethoxy-2-hexyn-yl(1)]-4-[3-oxo-(E)-1-octen-yl(1)]-pyrrolidone is carried out by column chromatography (silica gel/ethyl acetate).

Melting point: 70° C (ether)

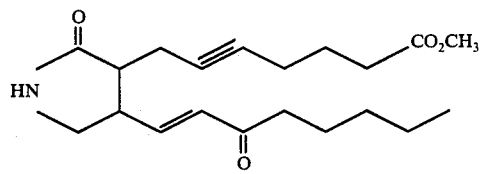

EXAMPLE 15

3-[6-Carbomethoxy-2-hexyn-yl(1)]-4-[3-oxo-3-cycloheptyl-(E)-1-propen-yl(1)]-pyrrolidone(2)

is obtained in a manner analogous to that in Example (14) by using dibutyl-[(2-oxo-2-cycloheptyl)-ethyl]-phosphonate. Melting point: 79°–80° C (ether)

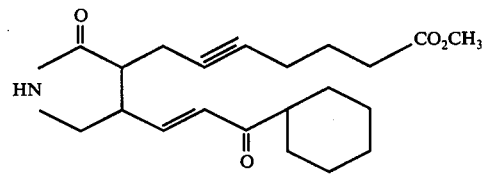

EXAMPLE 16

3-[6-Carbomethoxy-hexan-yl(1)]-4-[3-oxo-(E)-1-octen-yl(1)]-pyrrolidone(2)

is obtained in a manner analogous to that in Example (14) by using 3-[6-carbomethoxy-hexan-yl(1)]-4-hydroxymethyl-pyrrolidone (Example 10).

Melting point: 44°–44.5° C.

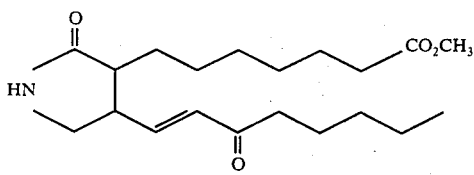

EXAMPLE 17

1-Phenyl-3-[6-carbomethoxy-2-hexyn-yl(1)]-4-[3-oxo-(E)-1-octen-yl(1)]-pyrrolidone(2)

is obtained in a manner analogous to that in Example (14) by using 1-phenyl-3-[6-carbomethoxy-2-hexyn-yl(1)]-4-hydroxymethyl-pyrrolidone(2) (Example 7) and dimethyl-(2-oxoheptyl)-phosphonate.

Rf: 0.76 (toluene/ethyl acetate = 2 : 1).

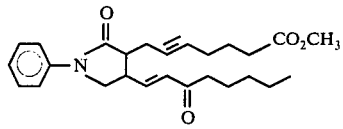

EXAMPLE 18

1-Phenyl-3-[6-carbomethoxy-hexan-yl(1)]-4-[5-ethoxy-4,4,-dimethyl-3-oxo-(E)-1-penten-yl(1)]-pyrrolidone(2)

is obtained in a manner analogous to that in Example (14) by using 1-phenyl-3-[6-carbomethoxy-hexan-yl(1)]-4-hydroxymethyl-pyrrolidone(2) (Example 11) and dimethyl-[(2-oxo-3-dimethyl-4-ethoxy)-butyl]-phosphonate.

Rf: 0.62 (ethyl actate/hexane = 1 : 10)

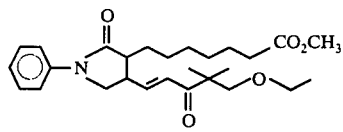

EXAMPLE 19

1-[4-(2',4'-Dichlorophenoxy)-phenyl]-3-[6-carbomethoxy-2-hexyn-yl(1)]-4-[3-oxo-(E)-1-octen-yl(1)]-pyrrolidone(2)

is obtained in a manner analogous to that in Example (4) by using 1-[4-(2',4'-dichlorophenoxy)-phenyl]-3-[6-carbomethoxy-2-hexyn-yl(1)]-4-hydroxymethyl-pyrrolidone(2).

Rf: 0.60 (toluene/ethyl acetate = 3 : 1)

EXAMPLE 20

1-Phenyl-3-[6-carbomethoxy-2-hexyn-yl(1)]-4-[3-oxo-4-(3'-trifluoromethylphenoxy)-(E)-1-buten-yl(1)]-pyrrolidone(2)

is obtained in a manner analogous to that in Example (14) by using 1-phenyl-3-[6-carbomethoxy-2-hexyn-yl(1)]-4-hydroxymethyl-pyrrolidone and dimethyl-[2-oxo-3-(3'-trifluoromethyl)-propyl]-phosphonate.

Rf: 0.87 (ether)

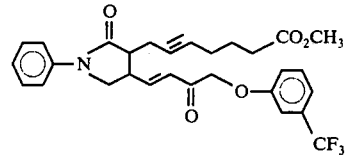

EXAMPLE 21

3-[6-Carbomethoxy-2-hexyn-yl(1)]-4-[3-oxo-4-[2-(3'-chloro)-phenoxy]-ethoxy-(E)-1-buten-yl(1)]-pyrrolidone(2)

is obtained in a manner analogous to that in Example (14) by using 3-[6-carbomethoxy-2-hexyn-yl(1)]-4-hydroxymethylpyrrolidone and dimethyl-[2-oxo-3-[2-(3'-chloro)-phenoxy]-ethoxy-propyl]-phosphonate.

Rf: 0.50 (ethyl acetate)

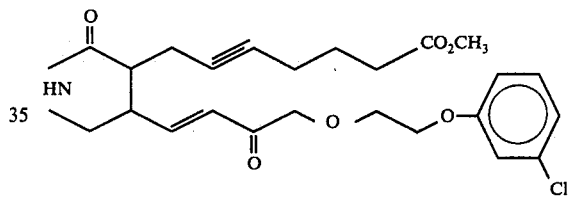

EXAMPLE 22

3-[6-Carbomethoxy-(Z)-2-hexen-yl(1)]-4-[3-oxo-(E)-1-octen-yl(1)]-pyrrolidone 310 mg of 3-[6-Carbomethoxy-2-hexyn-yl(1)]-4-[3-oxo-(E)-1-octen-yl(1)]-pyrrolidone in 20 ml of benzene and 0.1 ml of quinoline are hydrogenated with 20 mg of palladium on calcium carbonate (10% Pd), until the theoretical quantity of hydrogen has been absorbed. The benzene is then shaken with 2N H$_2$SO$_4$ to remove the quinoline. The residue remaining after removing the benzene is recrystallised from ether/petroleum ether. Melting point: 41°–42° C.

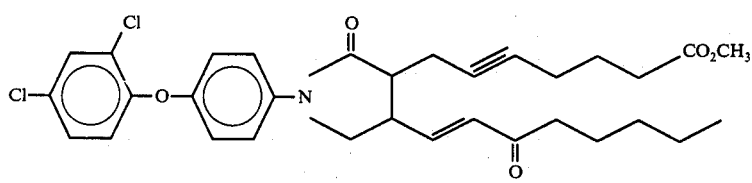

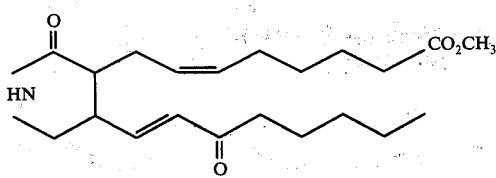

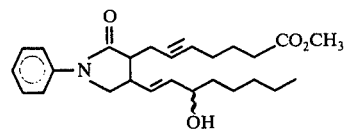

EXAMPLE 23

3-[6-Carbomethoxy-hexan-yl(1)]-4-[3-oxo-3-octan-yl(1)]-pyrrolidone 10 mg of PtO$_2$ are added to 714 mg of 3-[6-carbomethoxy-2-hexyn-yl(1)]-4-[3-oxo-(E)-1-octen-yl(1)]-pyrrolidone in 20 ml of benzene and hydrogenation is effected until there is no further absorption of hydrogen. The mixture is then filtered, concentrated and the residue recrystallised from ether/petroleum ether.

Melting point: 49°–50° C.

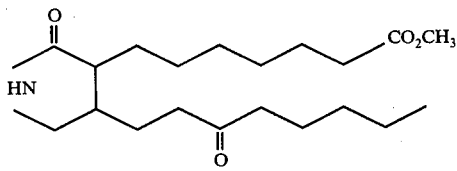

EXAMPLE 24

1-[4-(2′,4′-Dichlorophenoxy)-phenyl]-3-[6-carbomethoxy-2-hexyn-yl(1)]-4-[3-(RS)-hydroxy-(E)-1-octen-yl(1)]-pyrrolidone 15 ml of a 0.84 molar Zn(BH$_4$)$_2$ solution are added dropwise at 0° C to a solution of 2.5 g of 1-[4-(2′,4′-dichlorophenoxy)-phenyl]-3-[6-carbomethoxy-2-hexyn-yl(1)]-4-[3-oxo-(E)-1-octen-yl(1)]-pyrrolidone (Example 19) in 25 ml of absolute dimethoxyethane, and the whole is stirred for 2.5 hours at room temperature. 2N H$_2$SO$_4$ is added until a pH of 5 is reached, stirring is carried out briefly, and subsequently buffering with saturated sodium bicarbonate solution to a pH of 7. The filtered solution is evaporated in vacuo and the residue is extracted three times with 100 ml of methylene chloride each time. The organic phase is dried and evaporated in vacuo. The remaining oil is purified by means of column chromatography (silica gel; ethyl acetate/toluene = 1 : 2).

Rf: 0.24 and 0.28 (toluene/ethyl acetate = 3 : 1) (diastereoisomer mixture)

EXAMPLE 25

1-Phenyl-3-[6-carbomethoxy-2-hexyn-yl(1)]-4-[3-(RS)-hydroxy-(E)-1-octen-yl(1)]-pyrrolidone is obtained in a manner analogous to that in Example 24 by using 1-phenyl-3-[6-carbomethoxy-2-hexyn-yl(1)]-4-[3-oxo-(E)-1-octen-yl(1)]-pyrrolidone (Example 17). Rf: of the diastereoisomer mixture: 0.19 and 0.22 (toluene/ethyl acetate = 3 : 1).

EXAMPLE 26

3-[6-Carboxyisopropyl-2-hexyn-yl(1)]-4-[3-(RS)-hydroxy-3-cycloheptyl-(E)-1-propen-yl(1)]-pyrrolidone.

600 mg of 3-[6-carbomethoxy-2-hexyn-yl(1)]-4-[3-oxo-3-cycloheptyl-(E)-1-propen-yl(1)]-pyrrolidone (2) Example (15) are added to a solution of 2 g of aluminium triisopropylate in 10 ml of absolute isopropanol and 6 ml of toluene, and the whole is boiled. In the course of 2 hours, 8 ml are distilled off and the solution is cooled to room temperature. Subsequently ice is added and acidification effected with 2 N H$_2$SO$_4$. The reaction products are then extracted with CH$_2$Cl$_2$. After drying and concentrating the methylene chloride phase, the syrup obtained is purified over a column (silica gel/ethyl acetate).

Melting point: 47°–50° C (diastereoisomer mixture)

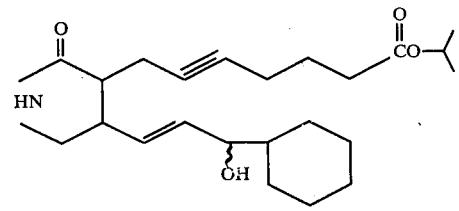

EXAMPLE 27

3-[6-Carbomethoxy-hexan-yl(1)]-4-[3-(RS)-hydroxy-octan-yl(1)]-pyrrolidone 1000 mg of 3-[6-Carbomethoxy-2-hexan-yl(1)]-4-[3-oxo-3-octen-yl(1)]-pyrrolidone (Example 23) in 10 ml of dimethoxyethane are added to 150 mg of Na(BH$_4$) in 15 ml of dimethoxyethane and the whole is stirred for 4 hours. 2N H$_2$SO$_4$ is then added dropwise, while cooling with ice, until there is a slightly acid reaction. Subsequently 2 g of KF in 3 ml of H$_2$O are added, then sodium bicarbonate solution until alkaline reaction. The solution remaining after filtration is evaporated and the

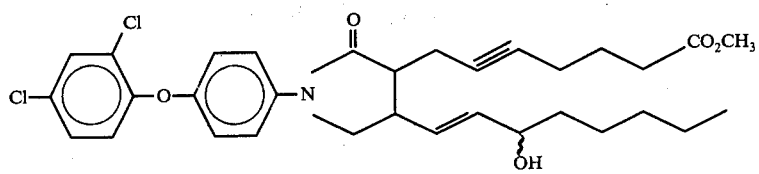

residue is purified over a silica gel column with ethyl acetate.

Rf: 0.33 (ethyl acetate)

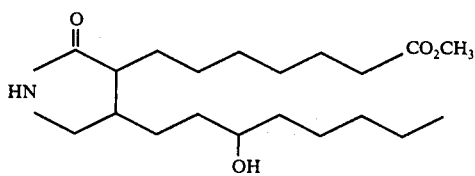

EXAMPLE 28

1-Hydroxymethyl-3-[6-carbomethoxy-hexan-yl(1)]-4-[3-(RS)-hydroxy-octan-yl(1)]-pyrrolidone 1 ml of 33% formalin and 20 mg of NaOH are added to 150 mg of 3-[6-carbomethoxy-hexan-yl(1)]-4-[3-(RS)-hydroxy-(E)-1-octan-yl(1)]-pyrrolidone from Example (27) in 1 ml of methanol. After 5 hours, neutralisation is effected with glacial acetic acid, the mixture is concentrated to a syrup and purification is effected over a column (silica gel/ethyl acetate).

Rf: 0.71 (ethyl acetate)

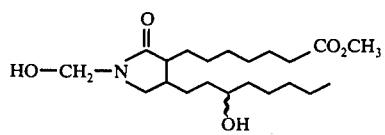

In accordance with the same process, in particular the following compounds of formula I or the corresponding acids and their physiologically tolerable amine and metal salts can be produced:

(29) 1-Phenyl-3-[6-carbomethoxy-(Z)-2-hexen-yl(1)]-4-[3-(RS)-hydroxy-(E)-1-octen-yl(1)]-pyrrolidone

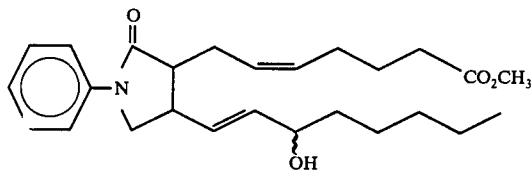

(30) 1-Phenyl-3-[6-carbomethoxy-hexan-yl(1)]-4-[3-(RS)-hydroxy-(E)-1-octen-yl(1)]-pyrrolidone

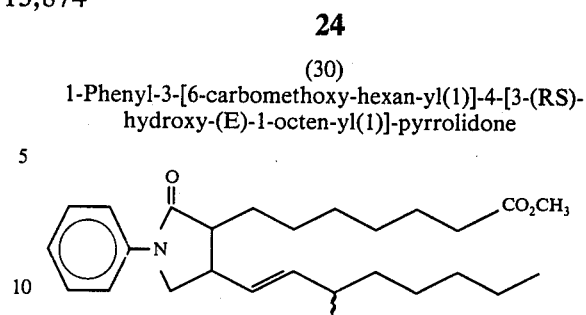

(31) 1-Phenyl-3-[6-carbomethoxy-hexan-yl(1)]-4-[3-(RS)-hydroxy-octan-yl(1)]-pyrrolidone

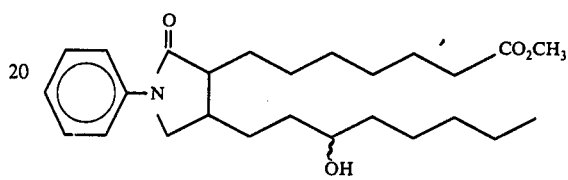

(32) 1-[4-(2',4'-Dichlorophenoxy)-phenyl]-3-[6-carbomethoxy-(Z)-2-hexen-yl(1)]-4-[3-(RS)-hydroxy-(E)-1-octen-yl(1)]-pyrrolidone

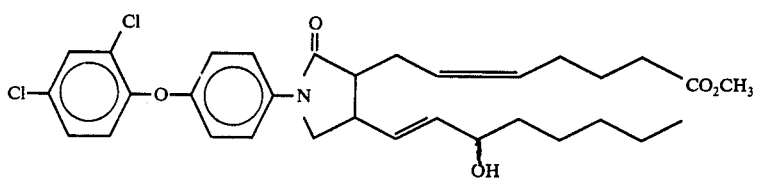

(33) 1-[4-(2',4'-Dichlorophenoxy)-phenyl]-3-[6-carbomethoxy-hexan-yl(1)]-4-[3-(RS)-hydroxy-(E)-1-octen-yl(1)]-pyrrolidone.

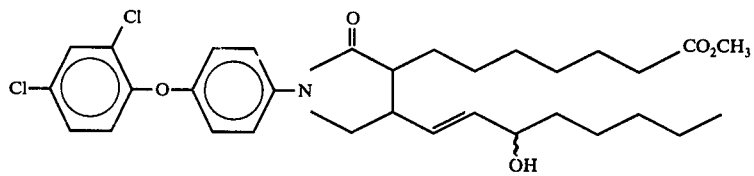

(34) 1-[4-(2',4'-Dichlorophenoxy)-phenyl]-3-[6-carbomethoxy-hexan-yl(1)]-4-[3-(RS)-hydroxy-octan-yl(1)]-pyrrolidone

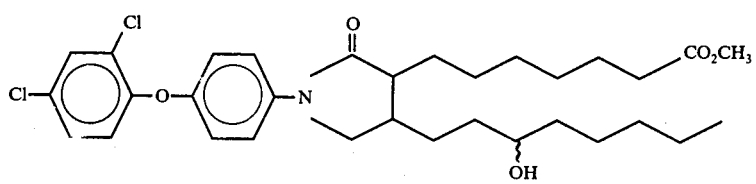

(35)

3-[6-Carboxyisopropyl-2-hexyn-yl(1)]-4-[3-(RS)-hydroxy-(E)-1-octen-yl(1)]-pyrrolidone

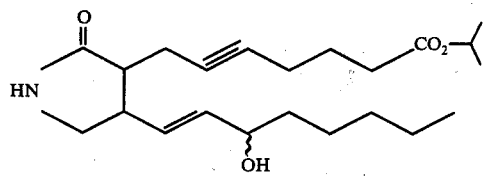

(36)

1-Hydroxymethyl-3-[6-carboxyisopropyl-2-hexyn-yl(1)]-4-[3-(RS)-hydroxy-(E)-1-octen-yl(1)]-pyrrolidone

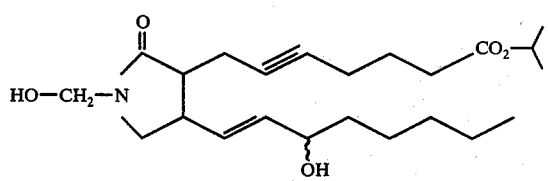

(37)

3-[6-Carboxyisopropyl-(Z)-2-hexen-yl(1)]-4-[3-(RS)-hydroxy-(E)-1-octen-yl(1)]-pyrrolidone

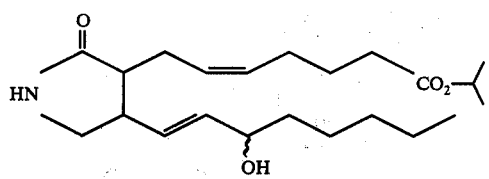

(38)

1-Hydroxymethyl-3-[6-carboxyisopropyl-(Z)-2-hexen-yl(1)]-4-[3-(RS)-hydroxy-(E)-1-octen-yl(1)]-pyrrolidone

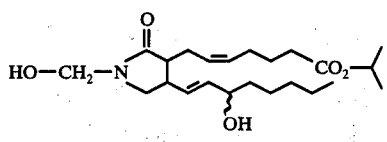

(39)

3-[6-Carboxyisopropyl-2-hexyn-yl(1)]-4-[3-(RS)-hydroxy-3-butyl-(E)-1-propen-yl(1)]-pyrrolidone (2)

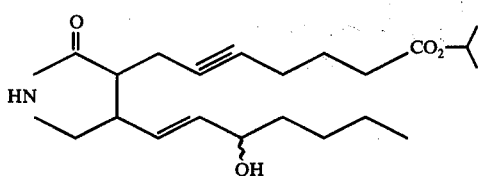

(40)

1-Hydroxymethyl-3-[carboxyisopropyl-2-hexyn-yl(1)]-4-[3-(RS)-hydroxy-3-butyl-(E)-1-propen-yl(1)]-pyrrolidone (2)

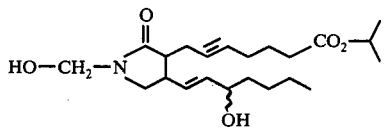

(41)

3-[6-Carboxyisopropyl-(Z)-2-hexen-yl(1)]-4-[3-(RS)-hydroxy-3-butyl-(E)-1-propen-yl(1)]-pyrrolidone (2)

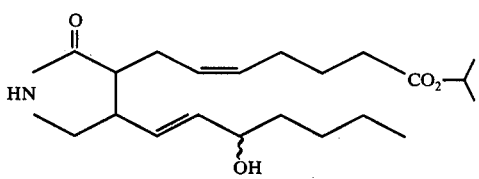

(42)

1-Hydroxymethyl-3-[6-carboxyisopropyl-(Z)-2-hexen-yl(1)]-4-[3-(RS)-hydroxy-3-butyl-(E)-1-propen-yl(1)]-pyrrolidone (2)

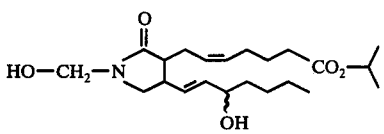

(43)

3-[6-Carboxyisopropyl-hexan-yl(1)]-4-[3-(RS)-hydroxy-3-butyl-(E)-1-propen-yl(1)]-pyrrolidone (2)

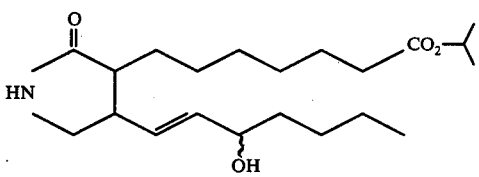

(44)

1-Hydroxymethyl-3-[6-carboxyisopropyl-hexan-yl(1)]-4-[3-(RS)-hydroxy-3-butyl-(E)-1-propen-yl(1)]-pyrrolidone (2)

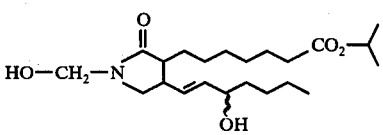

(45)
3-[6-Carboxyisopropyl-hexan-yl(1)]-4-[3-(RS)-hydroxy-heptan-yl(1)]-pyrrolidone (2)

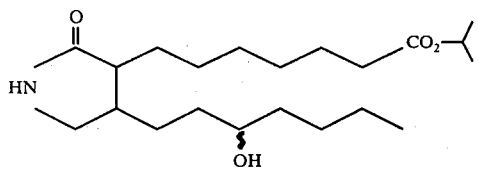

(46)
1-Hydroxymethyl-3-[6-carbomethoxy-hexan-yl(1)]-4-[3-(RS)-hydroxy-heptan-yl(1)]-pyrrolidone (2)

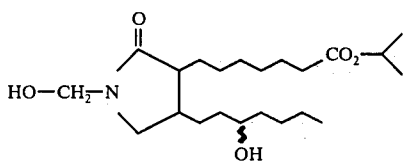

(47)
3-[6-Carboxyisopropyl-2-hexyn-yl(1)]-4-[3-(RS)-hydroxy-3-hexyl-(E)-1-propen-yl(1)]-pyrrolidone (2)

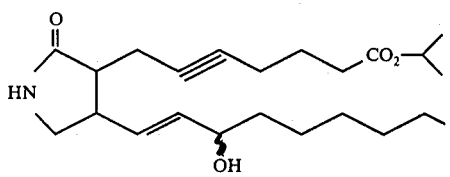

(48)
1-Hydroxy-methyl-3-[carboxyisopropyl-2-hexyn-yl(1)]-4-[3-(RS)-hydroxy-3-hexyl-(E)-1-propen-yl(1)]-pyrrolidone (2)

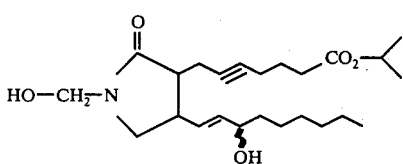

(49)
3-[Carboxyisopropyl-(Z)-2-hexen-yl(1)]-4-[3-(RS)-hydroxy-3-hexyl-(E)-1-propen-yl(1)]-pyrrolidone (2)

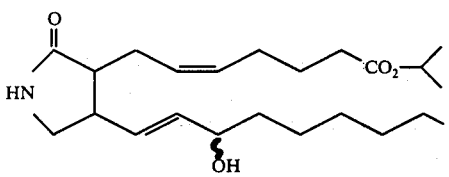

(50)
1-Hydroxymethyl-3-[carboxyisopropyl-(Z)-2-hexen-yl(1)]-4-[3-(RS)-hydroxy-3-hexyl-(E)-1-propen-yl(1)]-pyrrolidone (2)

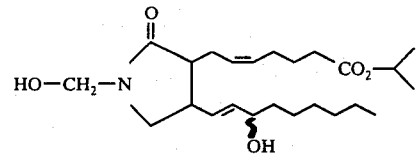

(51)
3-[6-Carboxyisopropyl-hexan-yl(1)]-4-[3-(RS)-hydroxy-3-hexyl-(E)-1-propen-yl(1)]-pyrrolidone (2)

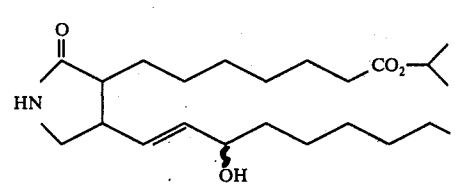

(52)
1-Hydroxymethyl-3-[6-carboxyisopropyl-hexan-yl(1)]-4-[3-(RS)-hydroxy-3-hexyl-(E)-1-propen-yl(1)]-pyrrolidone (2)

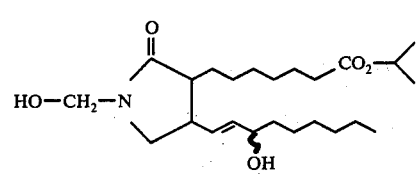

(53)
3-[6-Carboxyisopropyl-hexan-yl(1)]-4-[3-(RS)-hydroxy-nonan-yl(1)]-pyrrolidone (2)

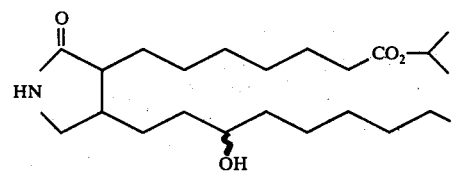

(54)
1-Hydroxymethyl-3-[6-carboxyisopropyl-hexan-yl(1)]-4-[3-(RS)-hydroxy-nonan-yl(1)]-pyrrolidone (2)

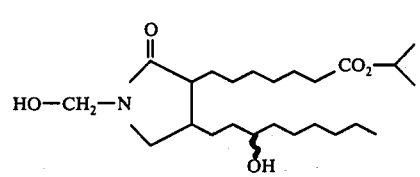

(55)
3-[6-Carboxyisopropyl-2-hexyn-yl(1)]-4-[3-(RS)-hydroxy-(E)-1-decen-yl(1)]-pyrrolidone (2)

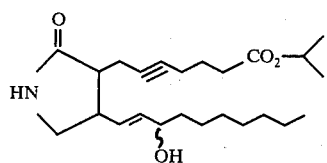

(56)
1-Hydroxymethyl-3-[carboxyisopropyl-2-hexyn-yl(1)]-4-[3-(RS)-hydroxy-(E)-1-decen-yl(1)]-pyrrolidone (2)

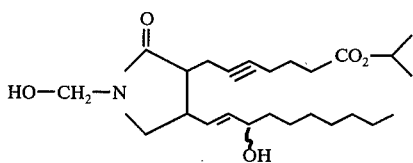

(57)
3-[6-Carboxyisopropyl-(Z)-2-hexen-yl(1)]-4-[3-(RS)-hydroxy-(E)-1-decen-yl(1)]-pyrrolidone (2)

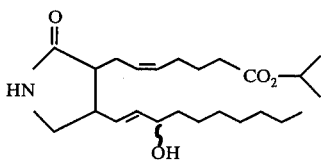

(58)
1-Hydroxymethyl-3-[6-carboxyisopropyl-(Z)-2-hexen-yl(1)]-4-[3-(RS)-hydroxy-(E)-1-decen-yl(1)]-pyrrolidone (2)

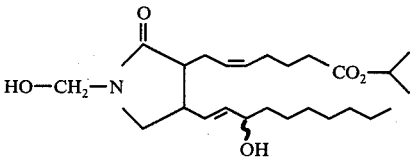

(59)
-[6-Carboxyisopropyl-hexan-yl(1)]-4-[3-(RS)-hydroxy-(E)-1-decen-yl(1)]-pyrrolidone (2)

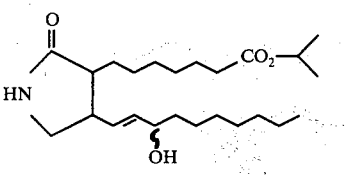

(60)
1-Hydroxymethyl-3-[6-carboxyisopropyl-hexan-yl(1)]-4-[3-(RS)-hydroxy-(E)-1-decen-yl(1)]-pyrrolidone (2

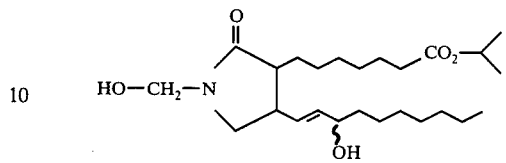

(61)
3-[6-Carboxyisopropyl-hexan-yl(1)]-4-[3-(RS)-hydroxy-decan-yl(1)]-pyrrolidone (2)

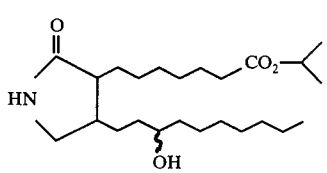

(62)
1-Hydroxymethyl-3-[6-carboxyisopropyl-hexan-yl(1)]-4-[3-(RS)-hydroxy-decan-yl(1)]-pyrrolidone (2)

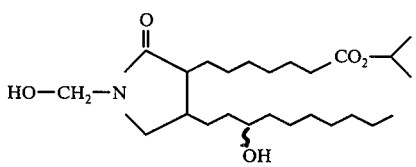

(63)
3-[6-Carboxyisopropyl-2-hexyn-yl(1)]-4-[3-(RS)-hydroxy-3-cyclohexyl-(E)-1-propen-yl(1)]-pyrrolidone (2)

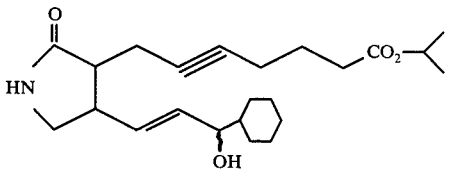

(64)
1-Hydroxymethyl-3-[6-carboxyisopropyl-2-hexyn-yl(1)]-4-[3-(RS)-hydroxy-3-cyclohexyl-(E)-1-propen-yl(1)]-pyrrolidone (2)

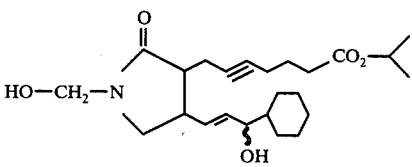

(65)
3-[6-Carboxyisopropyl-(Z)-2-hexen-yl(1)]-4-[3-(RS)-hydroxy-3-cyclohexyl-(E)-1-propen-yl(1)]-pyrrolidone (2)

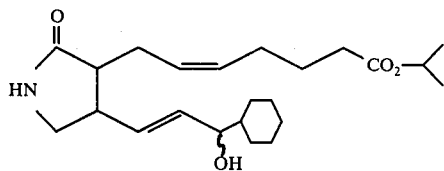

(66)
1-Hydroxymethyl-3-[6-carboxyisopropyl-(Z)-2-hexen-yl(1)]-4-[3-(RS)-hydroxy-3-cyclohexyl-(E)-1-propen-yl(1)]-pyrrolidone (2)

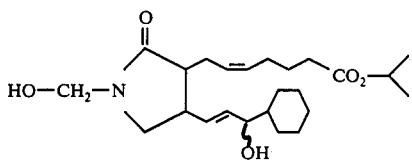

(67)
3-[6-Carboxyisopropyl-hexan-yl(1)]-4-[3-(RS)-hydroxy-3-cyclohexyl-(E)-1-propen-yl(1)]-pyrrolidone (2)

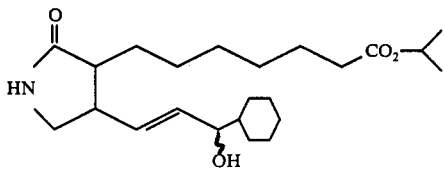

(68)
1-Hydroxymethyl-3-[carboxyisopropyl-hexan-yl(1)]-4-[3-(RS)-hydroxy-3-cyclohexyl-(E)-1-propen-yl(1)]-pyrrolidone (2)

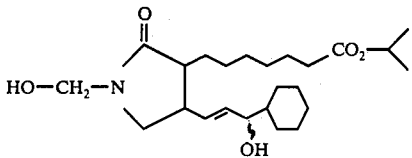

(69)
3-[6-Carboxyisopropyl-hexan-yl(1)]-4-[3-(RS)-hydroxy-3-cyclohexyl-propan-yl(1)]-pyrrolidone (2)

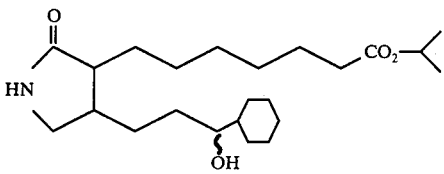

(70)
1-Hydroxymethyl-3-[6-carboxyisopropyl-hexan-yl(1)]-4-[3-(RS)-hydroxy-3-cyclohexyl-propen-yl(1)]-pyrrolidone (2)

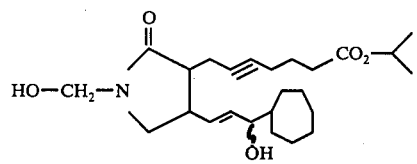

(71)
1-Hydroxymethyl-3-[6-carboxyisopropyl-2-hexyn-yl(1)]-4-[3-(RS)-hydroxy-3-cycloheptyl-(E)-1-propen-yl(1)]-pyrrolidone (2)

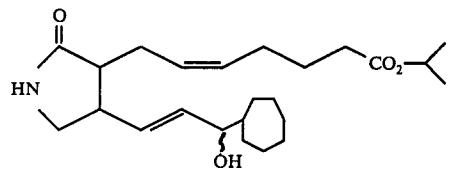

(72)
3-[6-Carboxyisopropyl-(Z)-2hexen-yl(1)]-4-[3-(RS)-hydroxy-3-cycloheptyl-(E)-1-propen-yl(1)]-pyrrolidone (2)

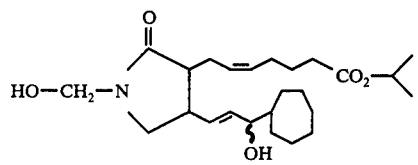

(73)
1-Hydroxymethyl-3-[6-Carboxyisopropyl-(Z)-2-hexen-yl(1)]-4-[3-(RS)-hydroxy-3-cycloheptyl-(E)-1-propen-yl(1)]-pyrrolidone

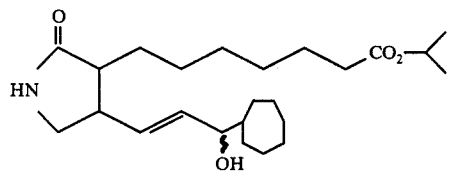

(74)
3-[6-Carboxyisopropyl-hexan-yl(1)]-4-[3-(RS)-hydroxy-3-cycloheptyl-(E)-1-propen-yl(1)]-pyrrolidone (2)

(75)

1-Hydroxy-methyl-3-[6-carboxyisopropyl-hexan-yl(1)]-
4-[3-(RS)-hydroxy-3-cycloheptyl-(E)-1-propen-yl(1)]-
pyrrolidone (2)

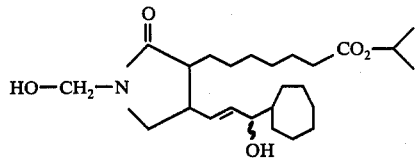

(76)

3-[6-Carboxyisopropyl-hexan-yl(1)]-4-[3-(RS)-hydroxy-
3-cycloheptyl-propan-yl(1)]-pyrrolidone (2)

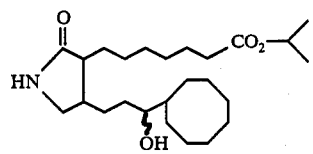

(77)

1-Hydroxymethyl-3-[6-carboxyisopropyl-hexan-yl(1)]-
4-[3-(RS)-hydroxy-3-cycloheptyl-propan-yl(1)]-pyrroli-
done (2)

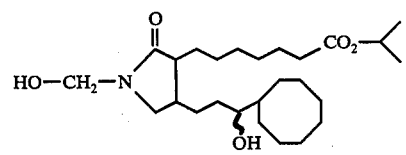

(78)

3-[6-Carboxyisopropyl-2-hexyn-yl(1)]-4-[3-(RS)-
hydroxy-4,4-dimethyl-5-ethoxy-(E)-1-penten-yl(1)]-
pyrrolidone (2)

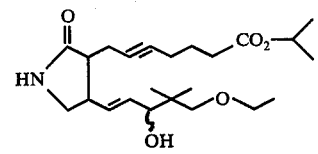

(79)

1-Hydroxymethyl-3-[6-carboxyisopropyl-2-hexyn-
yl(1)]-4-[3-(RS)-hydroxy-4,4-dimethyl-5-ethoxy-(E)-1-
penten-yl(1)]-pyrrolidone (2)

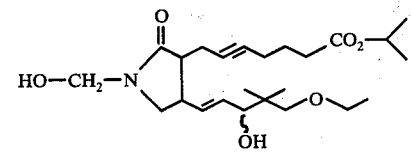

(80)

3-[6-Carboxyisopropyl-(Z)-2-hexen-yl(1)]-4-[3-(RS)-
hydroxy-4,4-dimethyl-5-ethoxy-(E)-1-penten-yl(1)]-
pyrrolidone (2)

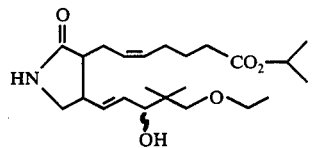

(81)

1-Hydroxymethyl-3-[6-carboxyisopropyl-(Z)-2-hexen-
yl(1)]-4-[3-(RS)-hydroxy-4,4-dimethyl-5-ethoxy-(E)-1-
penten-yl(1)]-pyrrolidone (2)

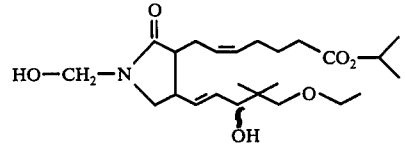

(82)

3-[6-Carboxyisopropyl-hexan-yl(1)]-4-[3-(RS)-hydroxy-
4,4-dimethyl-5-ethoxy-(E)-1-penten-yl(1)]-pyrrolidone
(2)

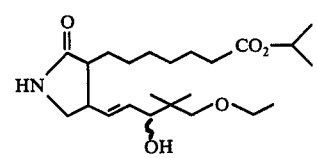

(83)

1-Hydroxymethyl-3-[6-carboxyisopropyl-hexan-yl(1)]-
4-[3-(RS)-hydroxy-4,4-dimethyl-5-ethoxy-(E)-1-penten-
yl(1)]-pyrrolidone (2)

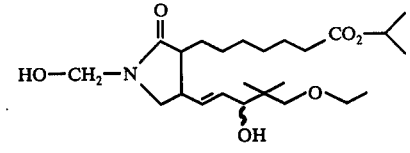

(84)

3-[6-Carboxyisopropyl-hexan-yl(1)]-4-[3-(RS)-hydroxy-
4,4-dimethyl-5ethoxy-pentan-yl(1)]-pyrrolidone (2)

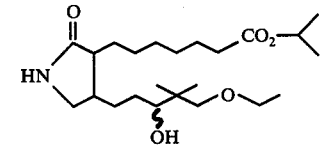

(85)

1Hydroxymethyl-3-[6-carboxyisopropyl-hexan-yl(1)]-4-[3-(RS)-hydroxy-4,4-dimethyl-5-ethoxy-pentan-yl(1)]-pyrrolidone (2)

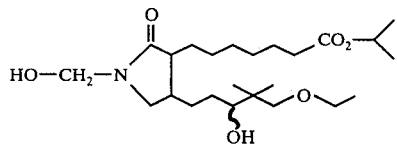

(86)

3-[6-Carboxyisopropyl-2-hexyn-yl(1)]-4-[3-(RS)-hydroxy-4-(3'-trifluoromethyl-phenoxy)-(E)-1-buten-yl(1)]-pyrrolidone (2)

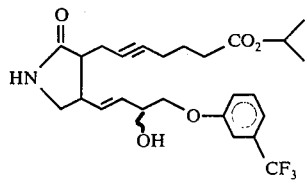

(87)

1-Hydroxymethyl-3-[6-carboxyisopropyl-2-hexyn-yl(1)]-4-[3-(RS)-hydroxy-4-(3'-trifluoromethyl-phenoxy)-(E)-1-buten-yl(1)]-pyrrolidone (2)

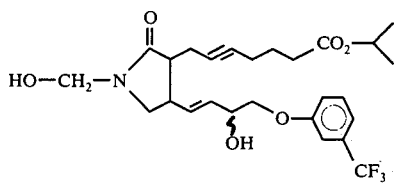

(88)

3-[6-Carboxyisopropyl-(Z)-2-hexen-yl(1)]-4-[3-(RS)-hydroxy-4-(3'-trifluoromethyl-phenoxy)-(E)-1-buten-yl(1)]-pyrrolidone(2)

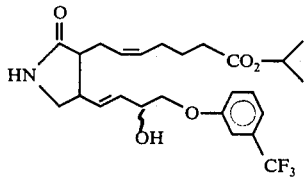

(89)

1-Hydroxymethyl-3-[6-carboxyisopropyl-(Z)-2-hexen-yl(1)]-4-[3-(RS)-hydroxy-4-(3'-trifluoromethyl-phenoxy)-(E)-1-buten-yl(1)]-pyrrolidone (2)

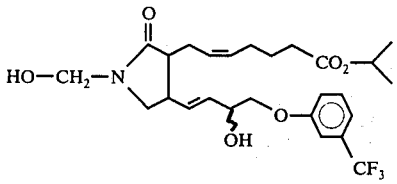

(90)

3-[6-Carboxyisopropyl-hexan-yl(1)]-4-[3-(RS)-hydroxy-4-(3'-trifluoromethyl-phenoxy)-(E)-1-buten-yl(1)]-pyrrolidone (2)

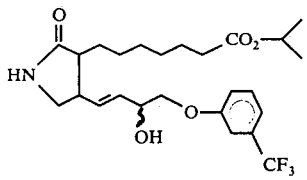

(91)

1-Hydroxymethyl-3-[6-carboxyisopropyl-hexan-yl(1)]-4-[3-(RS)-hydroxy-4(3'-trifluoromethyl-phenoxy)-(E)-1-buten-yl(1)]-pyrrolidone (2)

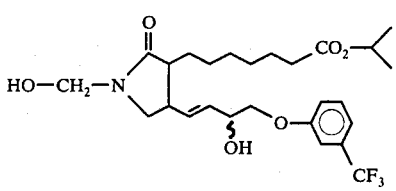

(92)

3-[6-carboxyisopropyl-hexan-yl(1)]-4-[3-(RS)-hydroxy-4-(3'-trifluoromethyl-phenoxy)-butan-yl(1)]-pyrrolidone (2)

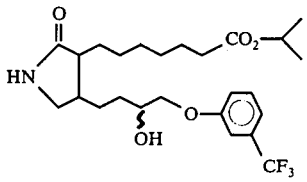

(93)

1-Hydroxymethyl-3-[6-carboxyisopropyl-hexan-yl(1)]-4-[3-(RS)-hydroxy-4-(3'-trifluoromethyl-phenoxy)-butan-yl(1)]-pyrrolidone (2)

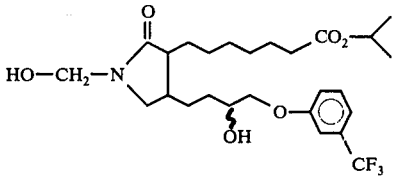

(94)

3-[6-Carboxyisopropyl-2-hexyn-yl(1)]-4-[3-(RS)-hydroxy-4-(4'-chlorophenoxy)-(E)-1-buten-yl(1)]-pyrrolidone (2)

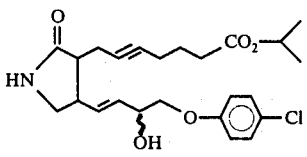

(95)
1-Hydroxymethyl-3-[6-carboxyisopropyl-2-hexyn-yl(1)]-4-[3-(RS)-hydroxy-4-(4'-chlorophenoxy)-(E)-1-buten-yl(1)]-pyrrolidone(2)

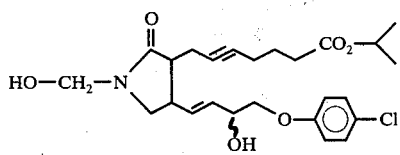

(96)
3-[6-Carboxyisopropyl-(Z)-2-hexen-yl(1)]-4-[3-(RS)-hydroxy-4-(4'-chlorophenoxy)-(E)-1-buten-yl(1)]-pyrrolidone (2)

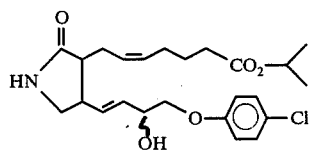

(97)
1-Hydroxymethyl-3-[6-carboxyisopropyl-(Z)-2-hexen-yl(1)]-4-[3-(RS)-hydroxy-4-(4'-chlorophenoxy)-(E)-1-buten-yl(1)]-pyrrolidone (2)

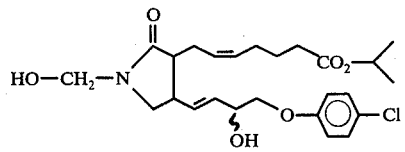

(98)
3-[6-Carboxyisopropyl-hexan-yl(1)]-4-[3-(RS)-hydroxy-4-(4'-chlorophenoxy)-(E)-1-buten-yl(1)]-pyrrolidone (2)

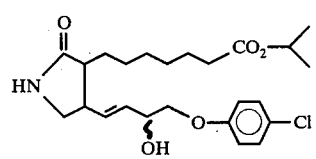

(99)
1-Hydroxymethyl-3-[6-carboxyisopropyl-hexan-yl(1)]-4-[3-(RS)-hydroxy-4-(4'-chlorophenoxy)-(E)-1-buten-yl(1)]-pyrrolidone (2)

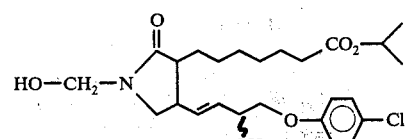

(100)
3-[6-Carboxyisopropyl-hexan-yl(1)]-4-[3-(RS)-hydroxy-4-(4'-chlorophenoxy)-butan-yl(1)]-pyrrolidone (2)

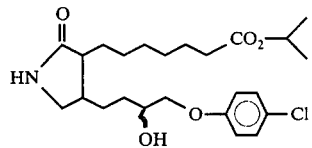

(101)
1-Hydroxymethyl-3-[6-carboxyisopropyl-hexan-yl(1)]-4-[3-(RS)-hydroxy-4-(4'-chlorophenoxy)-butan-yl(1)]-pyrrolidone

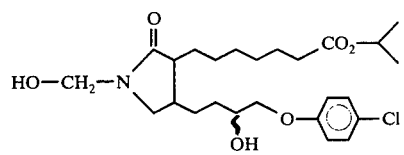

(102)
3-[6-Carboxyisopropyl-2-hexyn-yl(1)]-4-[3-(RS)-hydroxy-4-(3'-chlorophenoxy)-(E)-1-buten-yl(1)]-pyrrolidone (2)

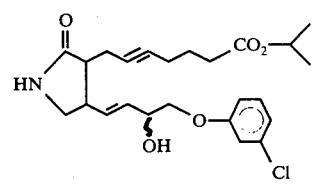

(103)
1-Hydroxymethyl-3-[6-carboxyisopropyl-2-hexyn-yl(1)]-4-[3-(RS)-hydroxy-4-(3'-chlorophenoxy)-(E)-1-buten-yl(1)]-pyrrolidone (2)

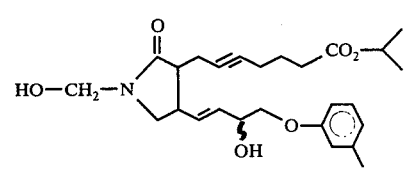

(104)
3-[6-Carboxyisopropyl-(Z)-2-hexen-yl(1)]-4-[3-(RS)-hydroxy-4-(3'-chlorophenoxy)-(E)-1-buten-yl(1)]-pyrrolidone (2)

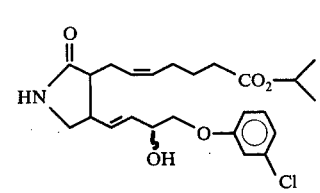

(105)

1-Hydroxymethyl-3-[6-carboxyisopropyl-(Z)-2-hexen-yl(1)]-4-[3-(RS)-hydroxy-4-(3'-chlorophenoxy)-(E)-1-buten-yl(1)]-pyrrolidone (2)

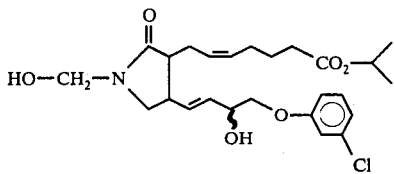

(106)

3-[6-Carboxyisopropyl-hexan-yl(1)]-4-[3-(RS)-hydroxy-4-(3'-chlorophenoxy)-(E)-1-buten-yl(1)]-pyrrolidone (2)

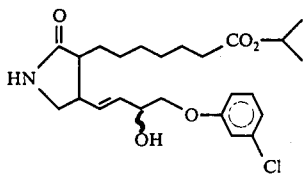

(107)

1-Hydroxymethyl-3-[6-carboxyisopropyl-hexan-yl(1)]-4-[3-(RS)-hydroxy-4-(3'-chlorophenoxy)-(E)-1-buten-yl(1)]-pyrrolidone (2)

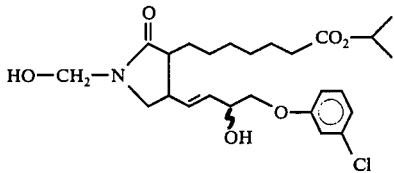

(108)

3-[6-Carboxyisopropyl-hexan-yl(1)]-4-[3-(RS)-hydroxy-4-(3'-chlorophenoxy)-butan-yl(1)]-pyrrolidone (2)

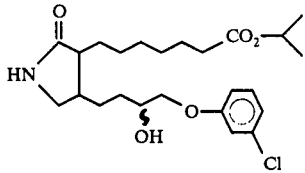

(109)

1-Hydroxymethyl-3-[6-carboxyisopropyl-hexan-yl(1)]-4-[3-(RS)-hydroxy-4-(3'-chlorophenoxy)-butan-yl(1)]-pyrrolidone (2)

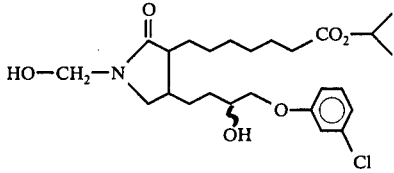

We claim:

1. A compound of the formula

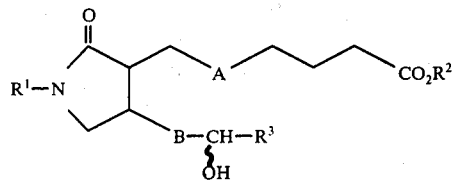

or a physiologically-compatible metal or amine salt of the free acid form thereof, wherein A is —$CH_2$—$CH_2$—, CH=CH-(cis), or —C≡C—;

B is —CH=CH— (trans) or, when A is —$CH_2$—$CH_2$—, is —CH=CH— (trans) or —$CH_2$—$CH_2$—;

$R^1$ is hydrogen, hydroxymethyl, phenyl, or phenyl substituted by straight-chain or branched alkyl having 1 to 4 carbon atoms, by halogen, by —S—alkyl or O-alkyl having 1 to 4 carbon atoms, by phenoxy, by halophenoxy, or by alkyl- or haloalkyl-phenoxy having 1 to 4 carbon atoms in the alkyl;

$R^2$ is hydrogen, alkyl having 1 to 5 carbon atoms, cycloalkyl having 3 to 8 carbon atoms, or phenylalkyl having 7 or 8 carbon atoms;

$R^3$ is straight-chain or branched alkyl having 1 to 10 carbon atoms or is such alkyl substituted by (a) —O-alkyl or —S-alkyl having 1 to 5 carbon atoms in the alkyl;

(b) phenoxy, halophenoxy, or alkyl- or haloalkyl-phenoxy having 1 to 3 carbon atoms in the alkyl, (c) —O-benzyl or —O-benzyl substituted by alkyl having 1 to 3 carbon atoms, (d) cycloalkyl, or (e) phenyl or alkylphenyl wherein the alkyl has 1 to 3 carbon atoms.

2. A pharmaceutical composition for inducing luteolysis or bronchospasmolysis, for inhibiting gastric juice secretion, or for combatting hypertension, said composition comprising a pharmaceutically-suitable carrier and a therapeutically-effective amount of a compound as in claim 1.

3. The method of effecting bronchodilation in a patient which comprises administering to said patient from 0.1 mg to 10 mg per day of a compound or salt as in claim 1.

4. The method of combatting hypertension in a patient which comprises administering to said patient from 1 mg to 10 mg per day of a compound or salt as in claim 1.

5. The method of inhibiting the secretion of gastric juice in a patient which comprises administering to said patient from 1 mg to 10 mg per day of a compound or salt as in claim 1.

6. A compound of the formula

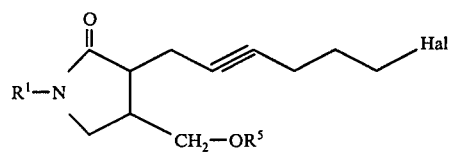

wherein Hal is chlorine or bromine, $R^5$ is allyl, benzyl, tert. butyl, chloromethyl, or an enol ether protective group, and $R^1$ is hydrogen, hydroxymethyl, phenyl, or phenyl substituted by straight-chain or branched alkyl having 1 to 4 carbon atoms, by halogen, by —S-alkyl or —O-alkyl having 1 to 4 carbon atoms, by phenoxy, by halophenoxy, or by alkyl- or haloalkyl-phenoxy having 1 to 4 carbon atoms in the alkyl.

7. A compound of the formula

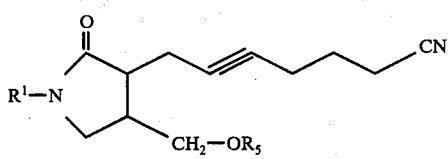

wherein R⁵ is allyl, benzyl, tert. butyl, chloromethyl, or an enol ether protective group and $R^1$ is hydrogen, hydroxymethyl, phenyl, or phenyl substituted by straight-chain or branched alkyl having 1 to 4 carbon atoms, by halogen, by —S— alkyl or —O-alkyl having 1 to 4 carbon atoms, by phenoxy, by halophenoxy, or by alkyl- or haloalkyl-phenoxy having 1 to 4 carbon atoms in the alkyl.

8. A compound of the formula

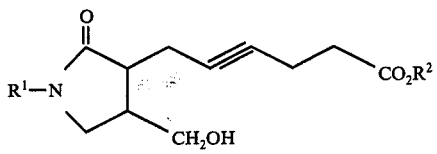

wherein $R^2$ is alkyl having 1 to 5 carbon atoms, cycloalkyl having 3 to 8 carbon atoms, or phenylalkyl having 7 or 8 carbon atoms, and $R^1$ is hydrogen, hydroxymethyl, phenyl, or phenyl substituted by straight-chain or branched alkyl having 1 to 4 carbon atoms, by halogen, by —S— alkyl or —O-alkyl having 1 to 4 carbon atoms, by phenoxy, by halophenoxy, or by alkyl- or haloalkyl-phenoxy having 1 to 4 carbon atoms in the alkyl.

9. A compound of the formula

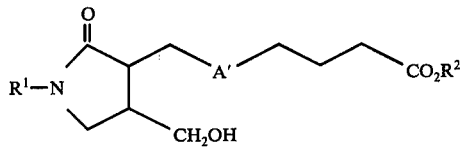

wherein

A' is —CH=CH-(cis) or —CH₂—CH₂—, $R^2$ is alkyl having 1 to 5 carbon atoms, cycloalkyl having 3 to 8 carbon atoms, or phenylalkyl having 7 or 8 carbon atoms, and $R^1$ is hydrogen, hydroxymethyl, phenyl, or phenyl substituted by straight-chain or branched alkyl having 1 to 4 carbon atoms, by halogen, by —S— alkyl or -O-alkyl having 1 to 4 carbon atoms, by phenoxy, by halophenoxy, or by alkyl- or haloalkyl-phenoxy having 1 to 4 carbon atoms in the alkyl.

10. A compound of the formula

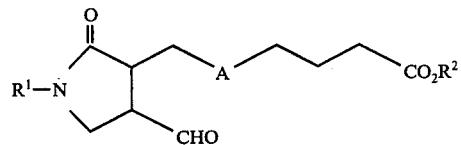

wherein

A is —CH₂—CH₂—, —CH=CH-(cis), or —CH≡CH—, $R^2$ is alkyl having 1 to 5 carbon atoms, cycloalkyl having 3 to 8 carbon atoms, or phenylalkyl having 7 or 8 carbon atoms, and $R^1$ is hydrogen, hydroxymethyl, phenyl, or phenyl substituted by straight-chain or branched alkyl having 1 to 4 carbon atoms, by halogen, by —S— alkyl or —O-alkyl having 1 to 4 carbon atoms, by phenoxy, by halophenoxy, or by alkyl- or haloalkyl-phenoxy having 1 to 4 carbon atoms in the alkyl.

11. A compound of the formula

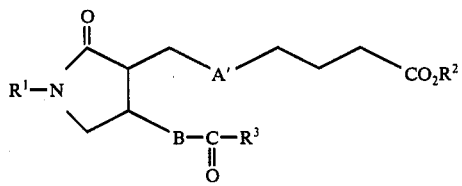

wherein

A' and B are both —CH₂—CH₂—, or A' is —CH=CH-(cis) and B is —CH=CH-(trans), wherein $R^3$ is straight-chain or branched alkyl having 1 to 10 carbon atoms or is such alkyl substituted by
(a) —O-alkyl or -S-alkyl having 1 to 5 carbon atoms in the alkyl;
(b) phenoxy, halophenoxy, or alkyl- or haloalkyl-phenoxy having 1 to 3 carbon atoms in the alkyl,
(c) -O-benzyl or O-benzyl substituted by alkyl having 1 to 3 carbon atoms,
(d) cycloalkyl, or
(e) phenyl or alkylphenyl wherein the alkyl has 1 to 3 carbon atoms;

$R^2$ is alkyl having 1 to 5 carbon atoms, cycloalkyl having 3 to 8 carbon atoms, or phenylalkyl having 7 or 8 carbon atoms, and $R^1$ is hydrogen, hydroxymethyl, phenyl, or phenyl substituted by straight-chain or branched alkyl having 1 to 4 carbon atoms, by halogen, by —S— alkyl or —O-alkyl having 1 to 4 carbon atoms, by phenoxy, by halophenoxy, or by alkyl- or haloalkyl-phenoxy having 1 to 4 carbon atoms in the alkyl.

12. A compound of the formula

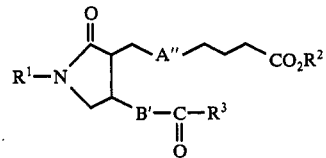

wherein

A'' and B' are both —CH₂—CH₂—;

$R^3$ is straight-chain or branched alkyl having 1 to 10 carbon atoms or is such alkyl substituted by
(a) —O-alkyl or —S-alkyl having 1 to 5 carbon atoms in the alkyl;
(b) phenoxy, halophenoxy, or alkyl- or haloalkyl-phenoxy having 1 to 3 carbon atoms in the alkyl,
(c) —O-benzyl or O-benzyl substituted by alkyl having 1 to 3 carbon atoms;
(d) cycloalkyl, or
(e) phenyl or alkylphenyl wherein the alkyl has 1 to 3 carbon atoms;

$R^2$ is alkyl having 1 to 5 carbon atoms, cycloalkyl having 3 to 8 carbon atoms, or phenylalkyl having 7 or 8 carbon atoms, and $R^1$ is hydrogen, hydroxymethyl, phenyl, or phenyl substituted by straight-chain or branched alkyl having 1 to 4 carbon atoms, by halogen, by —S— alkyl or -O-alkyl having 1 to 4 carbon atoms, by phenoxy, by halophenoxy, or by alkyl- or haloalkyl-phenoxy having 1 to 4 carbon atoms in the alkyl.

* * * * *